US006326147B1

(12) United States Patent
Oldham et al.

(10) Patent No.: US 6,326,147 B1
(45) Date of Patent: Dec. 4, 2001

(54) METHODS, APPARATUS, ARTICLES OF MANUFACTURE, AND USER INTERFACES FOR PERFORMING AUTOMATED BIOLOGICAL ASSAY PREPARATION AND MACROMOLECULE PURIFICATION

(75) Inventors: Mark Floyd Oldham, Los Gatos, CA (US); Peter Carlton Honebein, Reno, NV (US)

(73) Assignee: The Perkin-Elmer Corporation, Foster City, CA (US)

( * ) Notice: Subject to any disclaimer, the term of this patent is extended or adjusted under 35 U.S.C. 154(b) by 0 days.

(21) Appl. No.: 09/311,036

(22) Filed: May 13, 1999

(51) Int. Cl.[7] ....................................... C12Q 1/68
(52) U.S. Cl. ................. 435/6; 422/50; 435/91.2
(58) Field of Search ................. 435/6, 91.2, 65; 422/65

(56) References Cited

U.S. PATENT DOCUMENTS

| 5,104,621 |   | 4/1992  | Pfost et al. |         |
|-----------|---|---------|--------------|---------|
| 5,155,018 |   | 10/1992 | Gillespie et al. | 435/91 |
| 5,369,566 | * | 11/1994 | Pfost et al. | 364/147 |
| 5,580,728 | * | 12/1996 | Perlin | 435/91.2 |
| 5,665,539 | * | 9/1997  | Sano et al. | 435/6 |
| 5,885,529 | * | 3/1999  | Babson et al. | 422/65 |

FOREIGN PATENT DOCUMENTS

| WO 97/05248 | 2/1997 | (WO) . |
| WO 99/13976 | 3/1999 | (WO) . |
| WO 00/49557 | 8/2000 | (WO) . |

OTHER PUBLICATIONS

Hara et al. "Subtractive cDNA cloning using oligo(dT)30–latex PCR: isolation of cDNA clones specific to undifferentiated human embryonal cells" Nucleic Acids Research vol. 19, pp. 7097–7104, 1991.*

Guy Cathala, et al., *Laboratory Methods: A Method for Isolation of Intact, Translationally Active Ribonucleic Acid*, vol. 2, Nov. 1983, pp. 329–335.

Michael W. Clark, Ph.D., *Biomek 2000 Laboratory Automation Workstation: Modifying Pipetting Tool Specifications in BioWorks Software*, Beckman Instruments, Inc., 1996, 8 pages.

Stephen A. Krawetz, et al., *Isolation and Fractionation of Total Nucleic Acids from Tissues and Cells*, Journal of Biochemical and Biophysical Methods, 1986, pp. 29–36.

BioWorks Software, Document From the Internet: <http://www.beckmancoulter.com< (as of Apr. 29, 1999), 4 pages.

The Laboratory Robotics Interest Group Home, *Manufacturers of Robotics for Laboratory Automation*, Document From the Internet: <http://www.lab–robotics.org/manufact.htm,> (as of Apr. 29, 1999), 10 pages.

The Laboratory Robotics Interest Group Home, *Software and Information Management Providers for Laboratory*, Document From the Internet: <http:/lab–robotics,org/software.htm,> (as of May 8, 1999), 3 pages.

Qiagen Instruments, *Qiagen BioRobot 9600 System*, Document From the Internet: <http://www.qiagen.com/catalog/chapter 10,> (as of Aug. 25, 1999), 10 pages.

Qiagen Instruments, *New Qiagen BioRobot 9604 System*, Document From the Internet: <http://www.qiagen.com/catalog/chapter 10/chap10d.asp,> (as of May 8, 1999), 5 pages.

* cited by examiner

*Primary Examiner*—John S. Brusca
*Assistant Examiner*—Jeffrey S. Lundgren
(74) *Attorney, Agent, or Firm*—Finnegan, Henderson, Farabow, Garrett & Dunn L.L.P.

(57) ABSTRACT

Systems, methods, graphical user interfaces, and articles of manufacture consistent with the present invention allow for biological assay preparation and automated biological macromolecule purification. Consistent with the present invention, a user may instruct the system to perform a series of assay preparation and purification procedures. A user may choose a series of procedures to be performed by a single automated workstation, one after the other, without human intervention. A user may specify, for example, a combination of lysis, archive, purification, and isolation protocols, including polymerase chain reaction (PCR). For each chosen procedure, a user may select a standard protocol or create a new protocol. Parameters for each of the protocols are cross-checked against parameters of other chosen protocols and system hardware for physical and rational limitations.

18 Claims, 26 Drawing Sheets

RNA/DNA Archive Plate Protocol

Protocol Name [ABD Standard RNA Protocol]  In Use ☑

Source Tray(s) and DNA Precipitation | Transfer and First Filtration | Washes and Final Elution 1. Specify the Source Tray(s).

Lysate | Input 2 | Input 3
    Input Plate Type
    [Costar 96 well tray ▽]

2. Specify the DNA Precipitation conditions.

| | Add Buffer<br>uL | Number<br>of Mixes | Liquid Type |
    |---|---|---|---|
    | Initial DNA Buffer | 0 | 0 | [Water ▽] |
    | Second DNA Buffer | 0 | 0 | [Wash Buffer 2 ▽] |

[OK]  [Cancel]

FIG. 6

| RNA/DNA Archive Plate Protocol | ☒ |
|---|---|

Protocol Name [ABD Standard RNA Protocol]   In Use ☑

Source Tray(s) and DNA Precipitation [Transfer and First Filtration] Washes and Final Elution 3. Specify the conditions for transfering samples to the purification tray.

| | Add Buffer uL | Transfer uL | Number of Mixes | Starting uL | Liquid Type | Touchoff |
|---|---|---|---|---|---|---|
| Initial Transfer: | [None] | [200] | [4] | [250] | [Lysis Buffer ▽] | ☑ |
| Second Transfer: | [0] | [0] | [0] | | [Lysis Buffer ▽] | ☐ |

4. Specify lysis filtration conditions
☐ Fill All Wells

| | Incubation Temp | Incubation Minutes | Vacuum Seconds | Vacuum Level | Second Vacuum Seconds | Second Vacuum Level |
|---|---|---|---|---|---|---|
| Filtration Conditions | [25] | [0] | [120] | [7] | [0] | [7] |

[OK]  [Cancel]

FIG. 7

RNA/DNA Archive Plate Protocol

Protocol Name: [ABD Standard RNA Protocol]    In Use ☑

Source Tray(s) and DNA Precipitation | Transfer and First Filtration | [Washes and Final Elution]

5. Specify the washing conditions :

| Step | Use | Volume uL | Incubation Temp | Incubation Minutes | Vacuum Seconds | Vacuum Level | Second Vacuum Seconds | Second Vacuum Level | Liquid Type | Touchoff | Repeat # Times |
|---|---|---|---|---|---|---|---|---|---|---|---|
| ☑1. | RNAWash 1 | 400 | 25 | 0 | 120 | 7 | 0 | 7 | Wash Buffer 1 ▽ | ☑ | 1 |
| ☑2. | RNAWash 2 | 500 | 25 | 0 | 120 | 7 | 0 | 7 | Wash Buffer 2 ▽ | ☐ | 1 |
| ☑3. | RNAWash 2 | 300 | 25 | 0 | 120 | 10 | 90 | 20 | Wash Buffer 2 ▽ | ☑ | 2 |
| ☐4. | | | | | | | | | Water ▽ | ☐ | |
| ☐5. | | | | | | | | | Water ▽ | ☐ | |
| ☐6. | | | | | | | | | Water ▽ | ☐ | |
| ☐7. | | | | | | | | | Water ▽ | ☐ | |

6. Specify the Elution conditions.

| | 150 | 25 | | 30 | 7 | 0 | 7 | Water ▽ | | ☑ |

DNA: ☐ Create a DNA Filtrate Plate

[ OK ]    [ Cancel ]

FIG. 8

Dilution Archive Protocol

Protocol Name [ABD Single Tray 20:1]

In Use ☑

Specify the conditions for the Dilution Archive Plate(s).

Number of Mixes before sample transfer. [0]

| Plate | Dilution Factor | Initial Volume | Final Volume | Number of Mixes | Sample Liquid Type | Dilution Liquid Type |
|---|---|---|---|---|---|---|
| ☑ 1. | 1:20 ▽ | 200 ▽ uL | 200 uL | 2 | Water ▽ | Water ▽ |
| ☐ 2 | ▽ | ▽ uL | | 0 | Water ▽ | Water ▽ |

[ OK ]  [ Cancel ]

METHODS, APPARATUS, ARTICLES OF MANUFACTURE, AND USER INTERFACES FOR PERFORMING AUTOMATED BIOLOGICAL ASSAY PREPARATION AND MACROMOLECULE PURIFICATION

BACKGROUND OF THE INVENTION

1. Field of the Invention

The present invention relates to automated sample preparation for scientific research and, more particularly, to user interfaces, methods, apparatus and articles of manufacture for performing automated preparation of biological assays and biological macromolecule purification.

2. Background of the Invention

In the field of molecular biology, there is an ever increasing number of uses for isolated biological macromolecules, such as DNA, RNA, and proteins. Isolated biological macromolecules may be used, for example, in identifying genetic defects, diagnosing diseases, development of new drugs or treatments, and studying gene expression. Purified nucleic acids are derived from biological material samples, such as whole blood, plasma, blood serum, urine, feces, saliva, sperm, tissue, cells, and other body fluids, materials, or plant tissue.

There are many known methods for extracting biological macromolecules from biological materials. In fact, a number of specialized techniques have been developed for isolation and purification of DNA and RNA from various cell lines and tissue types. Most isolation and purification protocols, however, involve combinations and variations of a few basic steps.

Generally, the first step of an isolation protocol is to harvest tissue or collect cells from the biological material sample. A small portion of the biological material is placed in a container, such as a test tube or well of a multi-well tray. The sample is mixed with a lysis buffer solution that causes the cell structure of the biological material to break down and dissolve. This process is known as lysing. The type of lysis buffer used will depend on many factors including the type of biological material, the specific isolation protocol, and how the resulting biological macromolecule will be used once it is isolated.

After lysing, DNA, RNA, and proteins may be isolated from the lysed-cell mixture by, for example, precipitation, centrifugation, filtration, or affinity complex. Isolation protocols may also require multiple iterations of one or a combination of these techniques. Separation of the desired biological macromolecule may require, for example, that the mixture be incubated. The biological macromolecule may be separated from the liquid forming a precipitate or "pellet." The remaining fluid can then be aspirated, or pipetted, from the vial or well leaving the biological macromolecule, or the macromolecule may be filtered from the remaining fluid. Once the macromolecule is isolated from the biological material, it often must be further purified to remove the effects of the lysing materials. Additionally, for some uses, the isolated macromolecule may be diluted. Examples of conventional RNA, DNA, protein isolation and purification protocols may be found in the Kaufman et al., Handbook of Molecular and Cellular Methods in Biology and Medicine, CRC Press, 1995, pp. 1–63, which is expressly incorporated herein by reference. These processes and other concepts of molecular biology are discussed in more detail in Sambrook et al, Molecular Cloning: A Laboratory Manual, Cold Spring Harbor Laboratory Press ($2^{nd}$ Ed.), 1989, which is also expressly incorporated herein by reference.

The process of obtaining samples of DNA, RNA, and proteins in sufficient quantity for testing is a complicated and time intensive process. One experiment often requires the preparation of hundreds of samples, each of which may be prepared using slightly different control parameters. Historically, lab technicians have prepared trays or plates of multiple samples manually. A tray or plate may have any number of wells (eg. 12, 24, 48, 384, etc.) arranged in any configuration, however, a tray or plate having 96 vials or wells arranged in a 12×8 rectangular array is one popular arrangement. For each tray prepared, lab technicians must carefully record the exact, independent process used to prepare each of the wells.

The manual preparation of multi-well trays is therefore extremely tedious and, consequently, there have been numerous attempts to automate the process. Many manufacturers provide robotic devices for laboratory automation. These robotic devices frequently are pre-programmed to perform only a handful of specific functions and must be reprogrammed to perform other functions.

One automated laboratory workstation is the Biomek® 2000 Workstation by Beckman Instruments. The Biomek 2000 workstation is a liquid handling device controlled by using a Windows-based software interface called Bio-Works™. BioWorks allows the user to adjust pipetting specifications for the liquid handling tools or customize a tool for a special liquid transfer function. The Biomek 2000 workstation, however, requires the user either to use a provided protocol, or to custom develop an assay protocol by explicitly specifying all decisions and adjustments of a pipetting action well in advance of the activity. The user is not guided by the system when creating protocols or choosing protocol parameters. Additionally, the Biomek 2000 workstation does not create a database of parameters used by the technician or allow the technician to recall previously used parameters associated with an individual sample. Furthermore, the Biomek 2000 workstation does not perform cross-checking of parameters input by a user.

Other conventional products, like the BioRobot™ 9600 and 9604 Systems by Qiagen®, Inc., perform some automated liquid-handling tasks and purification protocols. These products, however, are designed to perform only a few of preprogrammed protocols at a time and are designed to prepare only one tray at a time. Following the completion of a protocol, a lab technician must manually remove or reposition the tray and reset the product to perform a secondary protocol. There is no cross-checking of parameters from one protocol to the next or between multiple trays.

Some conventional automated workstations allow users to create new protocols or modify existing protocols by modifying the parameters of, for example, type or quantity of liquid, length (in time) of incubation or mixing, or temperature of incubation. These conventional automated workstations do not, however, cross-check the parameters with a list of parameters recommended for specific parameters and therefore they allow the user to enter in parameters that may be in error. These modifications are done without any context to the desired protocol, such as prompting the user to enter parameters appropriate for the protocol. Furthermore, these conventional systems do not allow a user to easily specify different parameters for each separate well in a multi-well tray.

The increased use of isolated RNA, DNA, and proteins has created a need for automated methods for preparing sample trays and isolating DNA, RNA and proteins from biological materials samples that allow performance of multiple protocols in a sequence. There exists a need for an automatic workstation that allows for the rapid development of new protocols by focusing on the desired output of one or more protocols and not the individual steps required to achieve the desired output. There exists a further need for an automated workstation that allows for performance of multiple protocols on multiple trays. There exists a still further need for an intelligent automated workstation that helps avoid error by cross-checking parameters between multiple protocols in a sequence. There also exists a need for an automated workstation that allows a user to establish parameters for each vial or well in a multi-well sample tray.

SUMMARY OF THE INVENTION

Systems, methods, graphical user interfaces, and articles of manufacture consistent with the present invention perform automated sample procedures using a single robot. A user enters a set of protocol parameters which are then checked automatically for incompatibility with stored protocol parameters, previously entered protocol parameters, and hardware capabilities. If multiple automated sample procedures are chosen, the parameters chosen by the user for a first protocol are checked against the protocol parameters chosen for the other protocols. In response to computer instructions based on a first set of protocol parameters, a robot performs a procedure on a sample tray. If multiple automated sample procedures are chosen, the robot automatically performs a second procedure different from the first procedure, without human intervention following the first procedure, in response to computer instructions based on a second set of protocol parameters.

BRIEF DESCRIPTION OF THE DRAWINGS

The accompanying drawings, which are incorporated in and constitute a part of this specification, illustrate an embodiment of the invention and, together with the description, serve to explain the advantages and principles of the invention. In the drawings.

FIG. 6 shows an exemplary GUI consistent with the present invention;

FIG. 7 shows an exemplary GUI consistent with the present invention;

FIG. 8 shows an exemplary GUI consistent with the present invention;

FIG. 10 shows an exemplary GUI consistent with the present invention;

FIG. 13 shows an exemplary GUI consistent with the present invention;

FIGS. 16A and 16B show exemplary GUIs consistent with the present invention;

FIGS. 17A and 17B shows exemplary GUIs consistent with the present invention;

DETAILED DESCRIPTION

Reference will now be made in detail to an implementation consistent with the principles of the present invention as illustrated in the accompanying drawings. Wherever possible, the same reference numbers will be used throughout the drawings and the following description to refer to the same or like parts.

A. Introduction

Systems, methods, graphical user interfaces, and articles of manufacture consistent with the present invention allow for biological assay preparation and automated biological macromolecule purification. Consistent with the present invention, a user may instruct the system to perform a series of assay preparation and purification procedures. For example, after initial preparation of the sample, the sample may be lysed, purified, and archived. If RNA is obtained, a protocol to make cDNA may be performed. Optionally, the resulting RNA, DNA, or protein may be diluted. Another option is to use the isolated biological macromolecule in a known analysis process, such as polymerase chain reaction (PCR).

Each of these procedures may be performed according to one of many known protocols or according to a new protocol developed by the user during experimentation. Furthermore, these procedures may be used in combination with one another, that is, one procedure is used to produce a sample tray that is the input tray for another procedure. Methods, systems, and articles of manufacture consistent with the present invention perform automated biological assay preparation and biological macromolecule purification involving multiple successive procedures. The present invention discloses an "expert system" that guides a user in intelligently selecting appropriate parameters for a multi-protocol system. Such methods, systems, and articles of manufacture may utilize a series of graphical user interfaces (GUI) for receiving information, such as protocol parameters, from a user. Such methods, systems, and articles of manufacture cross-check the parameters entered by a user for errors and incompatibility, such as conflicts with known bounds for known protocols, conflicts with previous parameters entered by the user in other procedures of a combination, and protocols that exceed the system's capabilities. Such methods, systems, and articles of manufacture also allow importation, exploitation, and use of stored data from, for example, known protocols, previous experiments by the same or other users, or other sources.

B. Process

Figure 1A:
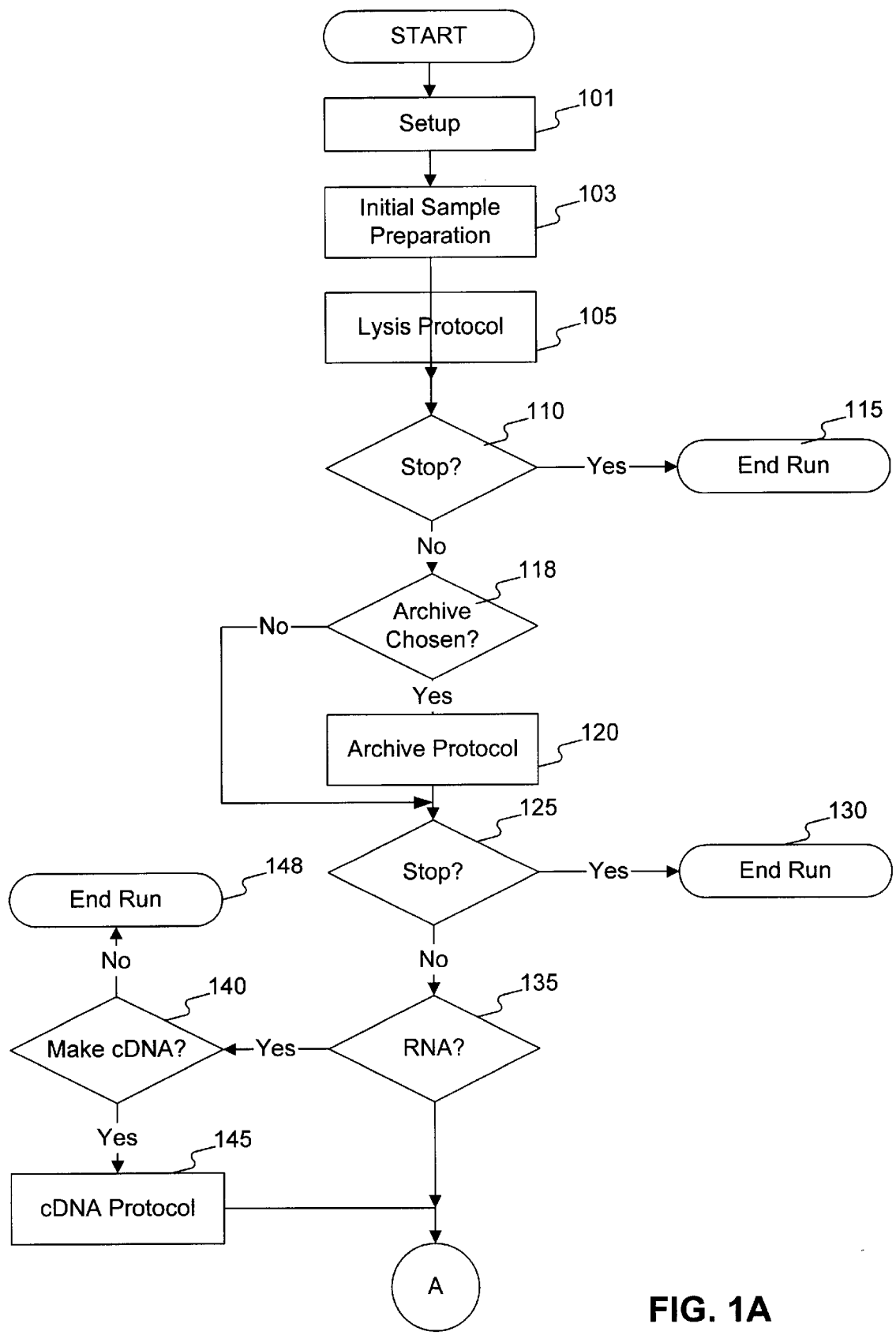
FIGS. 1A and 1B show a flow diagram of a method of performing automated sample tray preparation and biological macromolecule purification consistent with the present invention.
Figure 1B:
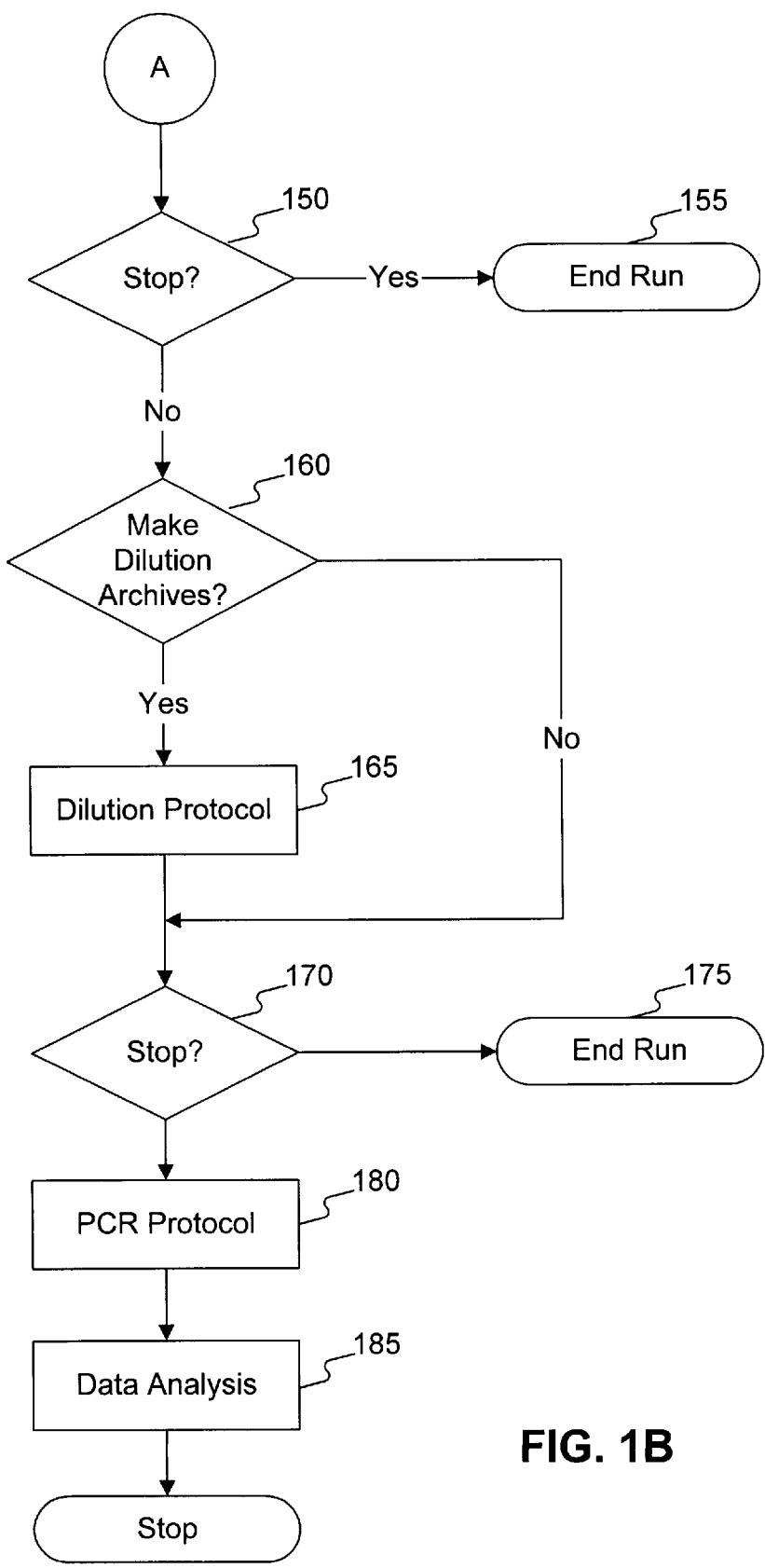

FIGS. 1A and 1B show a flow chart of a process consistent with the present invention. As shown in FIG. 1A, the process begins with a user setting up the automated workstation (step 101). Consistent with the present invention, the user may establish the set of procedures to be performed on each of multiple trays. The user may indicate a tray by, for example, entering in information by keyboard or clicking on a menu or tab in a graphical user interface (GUI). For each tray, a user may enter parameters defining the protocol or protocols to be performed on that tray for each of the chosen procedures. Alternatively, the user may choose to use parameters previously entered or imported from a database.

Figure 2A:
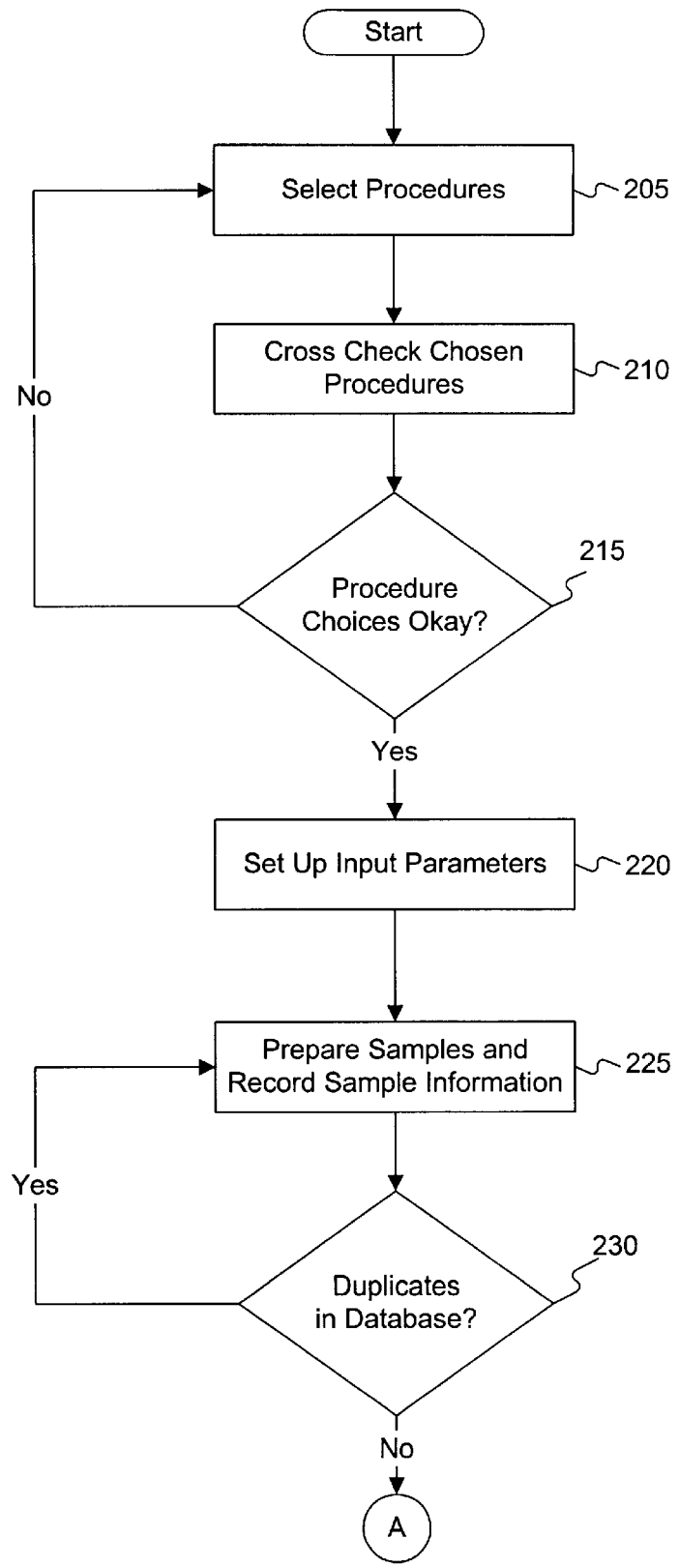
FIGS. 2A and 2B show a flow diagram of a set up process consistent with the present invention.
Figure 2B:
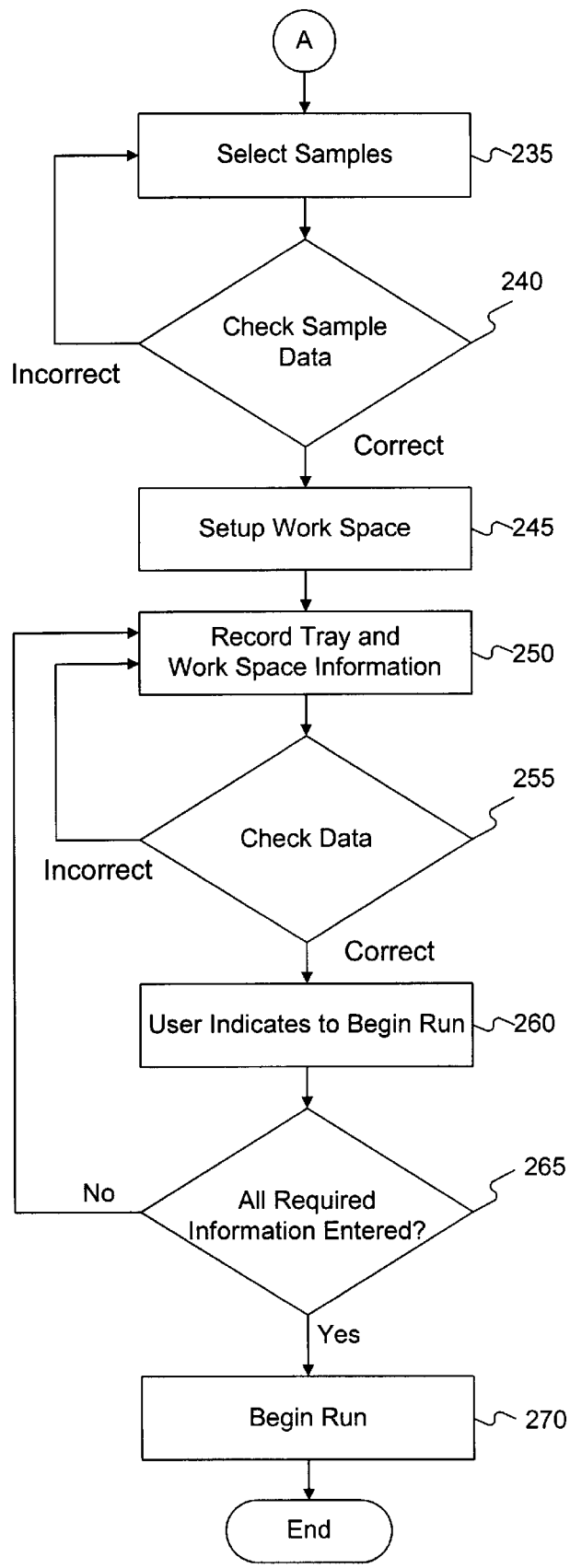
Figure 3:
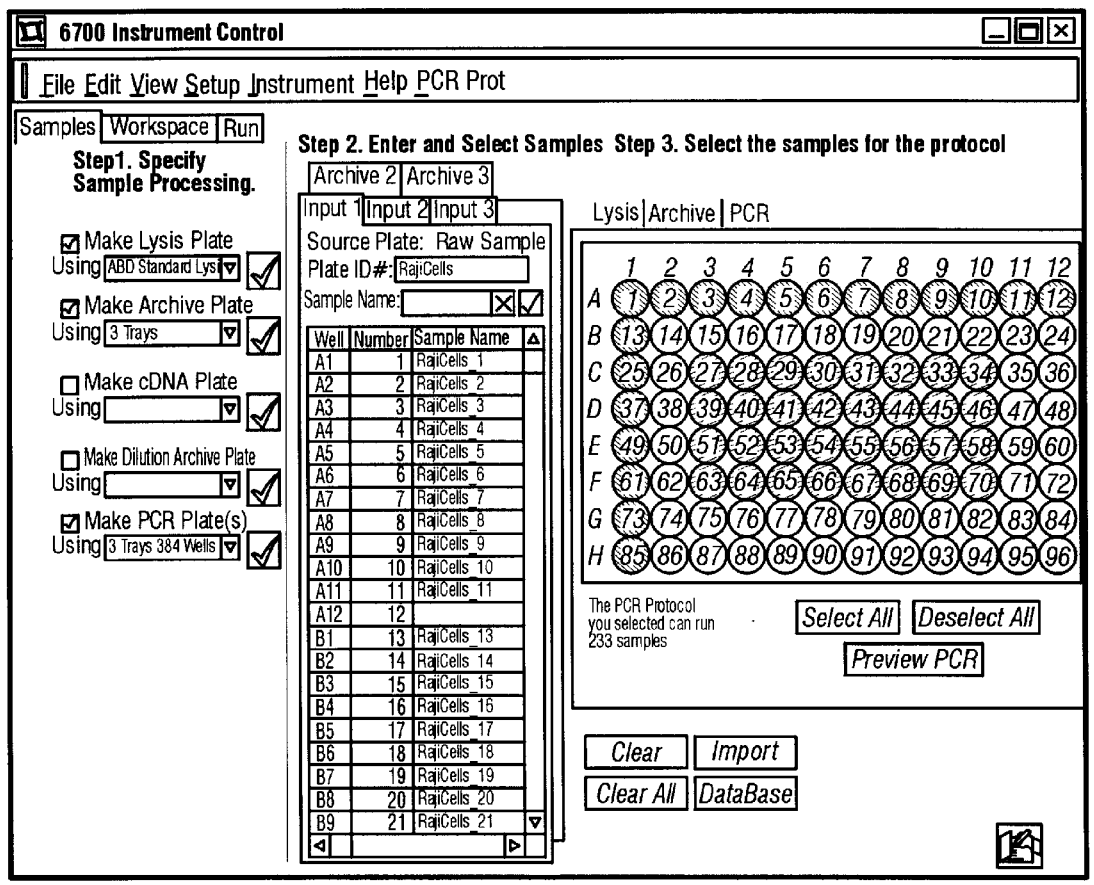
FIG. 3 shows an exemplary graphic user interface (GUI) consistent with the present invention.

FIGS. 2A and 2B illustrate a flow diagram of a setup process that can be performed for each tray consistent with step 101 of FIG. 1A. In step 205, the user selects at least one procedure to be performed on this sample tray. One example of a GUI consistent with the present invention is shown in FIG. 3. As shown on the left hand side of FIG. 3, the user may choose from a set of procedures that includes, for example, lysis, archive, make cDNA, dilution and PCR. The user chooses a procedure by, for example, clicking in the box to the left of the procedure. In FIG. 3, for example, the user has chosen the lysis, archive, and PCR procedures for this tray.

When a user selects or creates a protocol, the protocol is cross-checked for compatibility with, for example, the other protocols selected and the hardware capabilities of the associated automated work station (step 210). Such cross-checks may include, for example, checking to see that performance of the protocols does not require more trays or liquids than the system can accommodate or hold. The system also checks to see if it makes practical or scientific sense to perform any two or more protocols back-to-back. For example, if the user chooses to perform a cDNA protocol which seals the tray before performing its incubation steps, and the robot is incapable of removing the seal, it would be impractical to choose as a second protocol one that requires access to the contents of the tray. This combination would be incompatible and an error message will be displayed to the user.

Another example of incompatible protocol parameters is a combination of protocols that would result in more liquid than the capacity of the system. If the user chooses, for example, an Archive protocol, a dilution protocol, and a PCR protocol, the systems checks the volume used by each of these protocols, and determines whether there is sufficient capacity in the reagent reservoir. If the user chooses a combination of a cDNA protocol (requiring one tray), and a dilution protocol that creates two dilutions (thereby requiring two trays), the system may detect an incompatibility if the workstation can accommodate only two trays.

The system also checks across protocols to ensure that the output of one protocol is compatible with the expected input of the succeeding protocol. For example, if a lysis protocol (using two input trays, Input 1 and Input 2) is followed by an archive protocol (using two input trays, Input 1 and Input 3), Input 1 will be recorded as a "lysed sample" in the archive protocol, whereas Input 3 will be labeled a raw sample.

If at any time during setup, a protocol that was previously selected is then deselected by the user, the parameters for remaining protocols are modified as necessary to reflect the deselection. For example, in FIG. 3, a lysis, archive and PCR protocol are all selected. In accordance with these choices, a set of samples will be lysed, a subset of the lysed samples will be subjected to the archive protocol, and a subset of the archived samples will be used in the PCR protocol. If the lysis protocol is deselected, the input tray type will change from "Raw Sample" to "Lysed Sample," and the samples which are selected to be lysed, but not archived will be deselected. If, for example, the archive protocol is deselected, the user will be warned that the output of lysis protocol is lysed samples which cannot be used by the PCR protocol.

If the combination of procedures specified by the user is compatible (step 215), the user can select or create a particular protocol for each procedure (step 220). For each procedure, the system may automatically determine the type of input trays that are required automatically displays the information to the user by, for example, a GUI such as FIG. 3. For example, if the user chooses the archive procedure, each sample in the input tray must contain a lysate. If the user chooses to perform a PCR protocol, the appropriate input tray is an archive tray where the DNA or RNA has already been isolated.

For each of the procedures, the user may select a standard protocol, create a new protocol, or modify an existing or prior protocol. In FIG. 3, for example, the user may indicate a standard protocol by using the drop box to display choices and highlighting one of the choices. To create a new protocol, the user may, for example, highlight the word "New." Alternatively, the user may highlight a choice which recalls previously stored protocols. The user may specify parameters for new protocols or review and/or modify parameters for existing protocols. The user may be prompted for parameter information by one or more GUIs.

Depending on the procedures chosen, there may be multiple input trays. In the center column of FIG. 3, the example shows the contents of each well of an exemplary 96-well tray. The exemplary tray in FIG. 3 is the first of three archive trays. In the example shown in FIG. 3, the user may move between the three trays by clicking on graphical "tabs" labeled "Archive 1," "Archive 2," and "Archive 3." Within a chosen archive tray, the user may select from multiple recommended inputs for each individual well.

Figure 4:
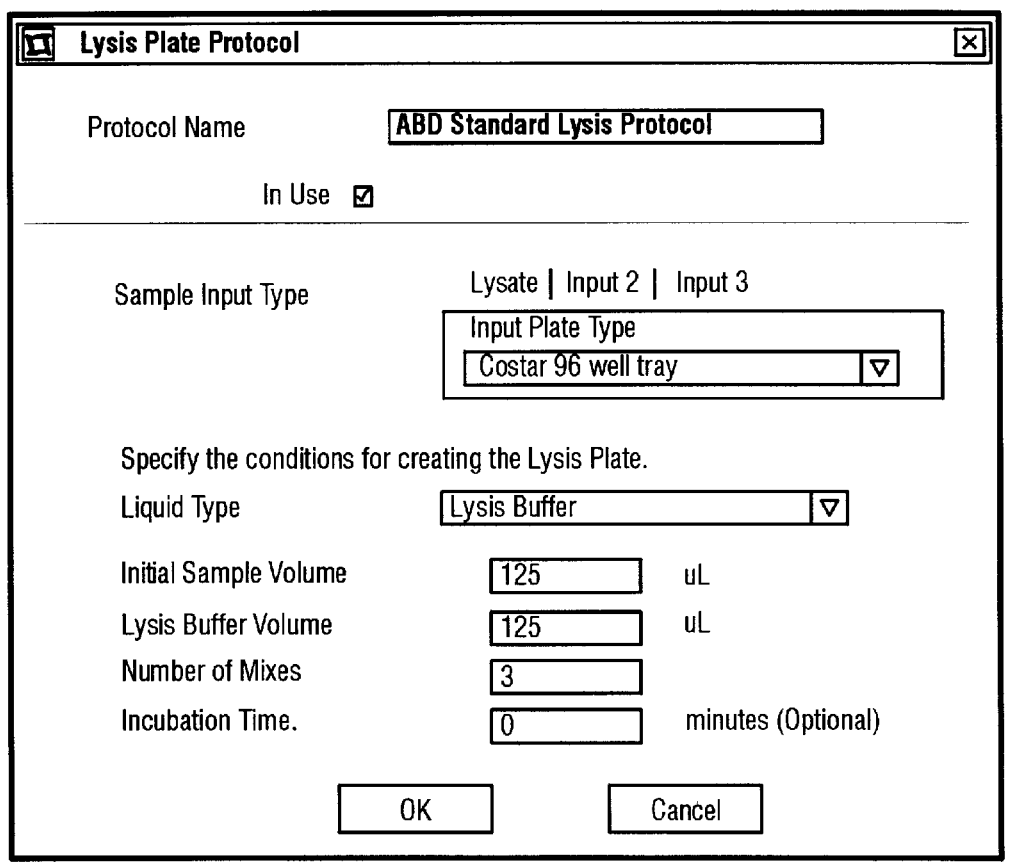
FIG. 4 shows an exemplary GUI consistent with the present invention.

If the user selected the lysis procedure in step 205, for example, a GUI like FIG. 4 may be displayed to the user. As shown in FIG. 4, the user may choose, for example, input tray type, liquid type, initial sample volume, lysis buffer volume, number of mixes, and incubation time. A "mix" is one or more chemicals added to the mixture to homogenize the mixture, encourage the separation of DNA into smaller pieces, and further degrade the cell walls to facilitate lysis. When the user has finished entering or modifying parameters for lysis, the parameters for this protocol are saved. Parameters are checked at the time they are entered or selected, producing error messages as appropriate. For example, during selection of lysis parameters, the sum of the buffer liquid volume and the initial sample volume are checked against the volume which the selected tray can hold. In addition, the volume of the buffer is checked against the maximum volume the tip can hold, compensating for air gaps, pump gain errors, and pump backlash compensation.

The user also may enter information that identifies the creator of the new protocol, such as a user name and/or password. If the protocol is new, the user may edit the protocol at any point in the setup process, until the protocol is used to produce samples. Once the protocol has been used, the protocol data cannot be edited and is saved for regulated market compliance purposes.

Figure 5A:
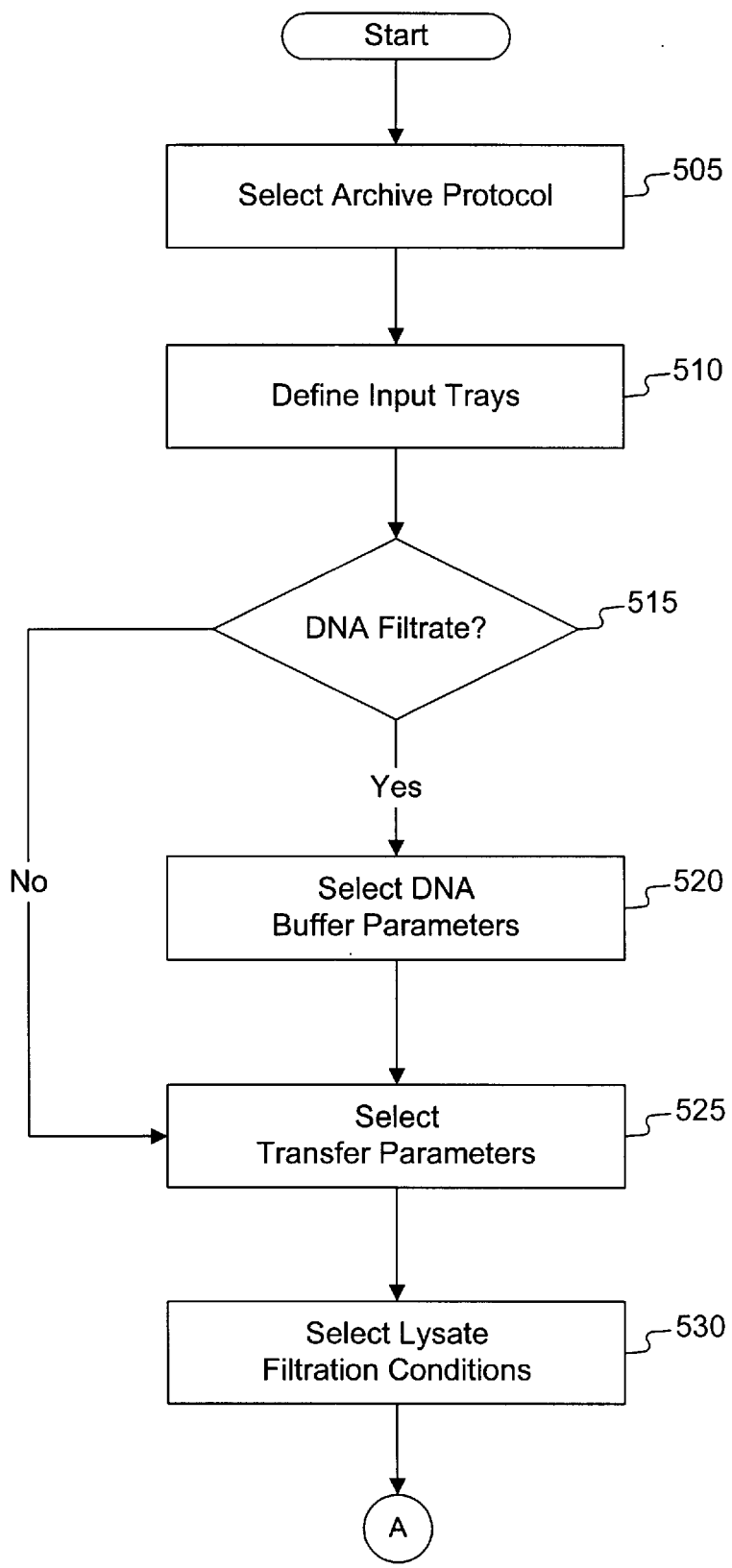
FIGS. 5A and 5B show a flow diagram of a process for creating new and modified archive protocols consistent with the present invention.
Figure 5B:
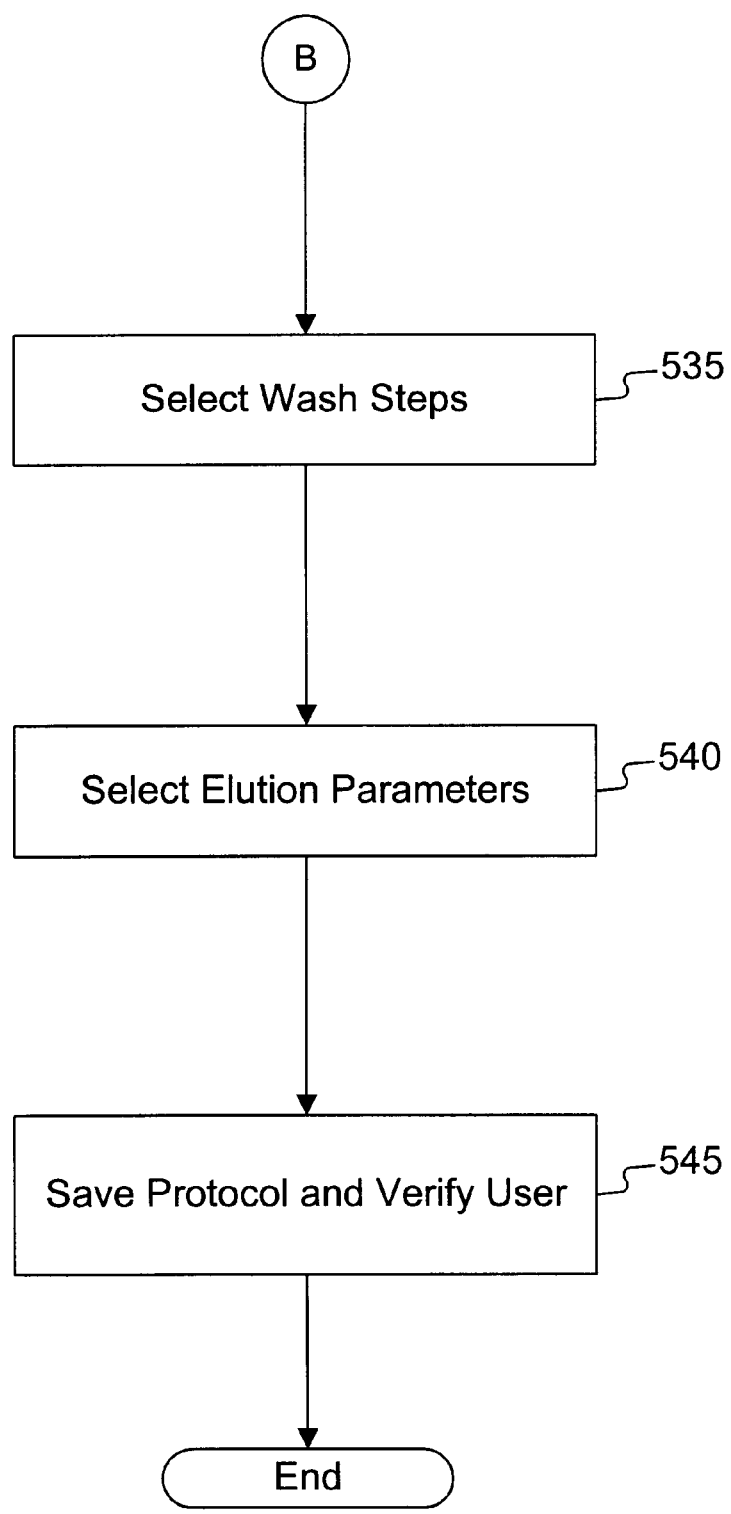

If the user selects the archive procedure, for example, the user may be prompted to enter information for creating a new or modified archive protocol. FIGS. 5A and 5B illustrate the steps of a process for creating a new or modified archive protocol consistent with the present invention. The process begins with selection of the archive procedure (step 505). FIGS. 6 through 8 are exemplary GUIs that may be displayed to the user to assist the user in defining a specific archive protocol. Users may, for example, define one or more input trays (step 510). If the input sample is a DNA filtrate (step 515), the user may optionally select DNA buffer parameters (step 520). As shown in FIG. 7, the user may specify a particular procedure for transferring samples to the purification tray (step 525). The user selects one or more sets of parameters, such as volume of liquid, number of mixes, liquid type, and touch-off. If there are multiple steps to the transfer procedure, there may be multiple sets of transfer parameters. Touch-off refers to the drip of liquid remaining on the tip of the purification tray following the vacuum stage. To reduce contamination, the vacuum station moves the purification trays so that the drip directors are gently touched against the sides of the tray beneath it to remove touch-off. The user also has an option to add an additional buffer to dilute the remaining liquid to recover more material from the well to get a higher percentage recovery of sample from the well.

In an archive protocol, the user may select lysate filtration conditions (step 530). In the prior step, a lysate was transferred to the purification tray. At this point, the user may choose parameters for an optional incubation period prior to filtration, such as time and temperature. The user also choose various filtration parameters, such as vacuum time and vacuum level. Additionally, the process allows the user to specify multiple vacuum stage parameter sets. If vacuuming is performed more than once, the user may specify multiple sets of vacuum parameters accordingly. At this point, with first lysate, the eluent (potentially membranes, proteins, etc.) will either by disposed of or, if the user wishes to recover other biological macromolecules from it, saved and transferred to another tray.

Next, the user selects at least one wash step (step 535). Washing is performed to further remove or dissolve impurities and/or liquid from a previous step. The user may choose various wash parameters, such as wash name (a label for the user's convenience), wash volume (how much of the new reagent that will be added to the purification tray), incubation period and temperature (prior to each wash step), vacuum time, vacuum level, and liquid type. Following each wash period, the eluent is vacuumed away and the sample remains in the purification tray. Touch-off may also be performed at this stage to prevent cross-contamination.

Following washing, the purified sample in the purification tray is transferred to an archive tray by elution. During elution, the sample is dissolved in an elution buffer. The user selects elution parameters, such as the type of liquid buffer, volume, incubation time, liquid type, incubation temperature, vacuum time, and vacuum level (step 540).

Once the user has completed entering parameters, the protocol is saved (step 545). The user also may enter information that identifies the creator of the new protocol, such as a user name and/or password. If the protocol is new, the user may edit the protocol at any point in the setup process, until the protocol is used to produce samples. Once the protocol has been used, however, the protocol data cannot be edited and is saved for regulated market compliance purposes.

Figure 9:
FIG. 9 shows an exemplary GUI consistent with the present invention.

If the user selected to make cDNA in step 205, the user selects a cDNA protocol. The user may select a standard protocol or choose to create a new protocol by specifying new parameters or modifying an existing protocol. The user may input information by, for example, a GUI as is shown in FIG. 9. Using a GUI like FIG. 9, or other means of entering information, the user chooses such parameters as protocol name, number of initial mixes used to homogenize the sample before transfer, volume of sample to be transferred, sample liquid type, total volume, amount of buffer to add, liquid type of added buffer, number of mixes to add these two things together, and whether the tray should be sealed before incubation steps, among other things. Additionally, the user may specify incubation temperatures and times for incubating the solution following the mixing of the master mix with the sample. Optionally, the user may specify a "stop solution" for use in killing the enzyme that does the conversion from RNA to cDNA.

When the user has finished entering parameters for making cDNA, the parameters for this protocol are saved. The user also may enter information that identifies the creator of the new protocol, such as a user name and/or password. If the protocol is new, the user may edit the protocol at any point in the setup process, until the protocol is used to produce samples. Once the protocol has been used, the protocol data cannot be edited and is saved for regulated market compliance purposes.

If the user selected dilution in step 205, the user selects a dilution protocol. An example of a GUI for assisting in the set up of dilution procedures is shown in FIG. 10. Dilution may be done on any purified biomolecule including a cDNA archive, DNA archive, RNA archive, or following a previous dilution. The dilution protocol begins with name, number of mixes from initial sample, sample liquid type, dilutant liquid type, number of dilution trays to be made, dilution factors for each tray, initial end volume, final volume. Initial end volume is the combined volume of diluent and sample prior to using some of that volume to create a subsequent dilution tray.

When the user has finished entering parameters for dilution, the parameters for this protocol are saved. The user also may enter information that identifies the creator of the new protocol, such as a user name and/or password. If the protocol is new, the user may edit the protocol at any point in the setup process, until the protocol is used to produce samples. Once the protocol has used, the protocol data cannot be edited and is saved for regulated market compliance purposes.

Figure 11A:
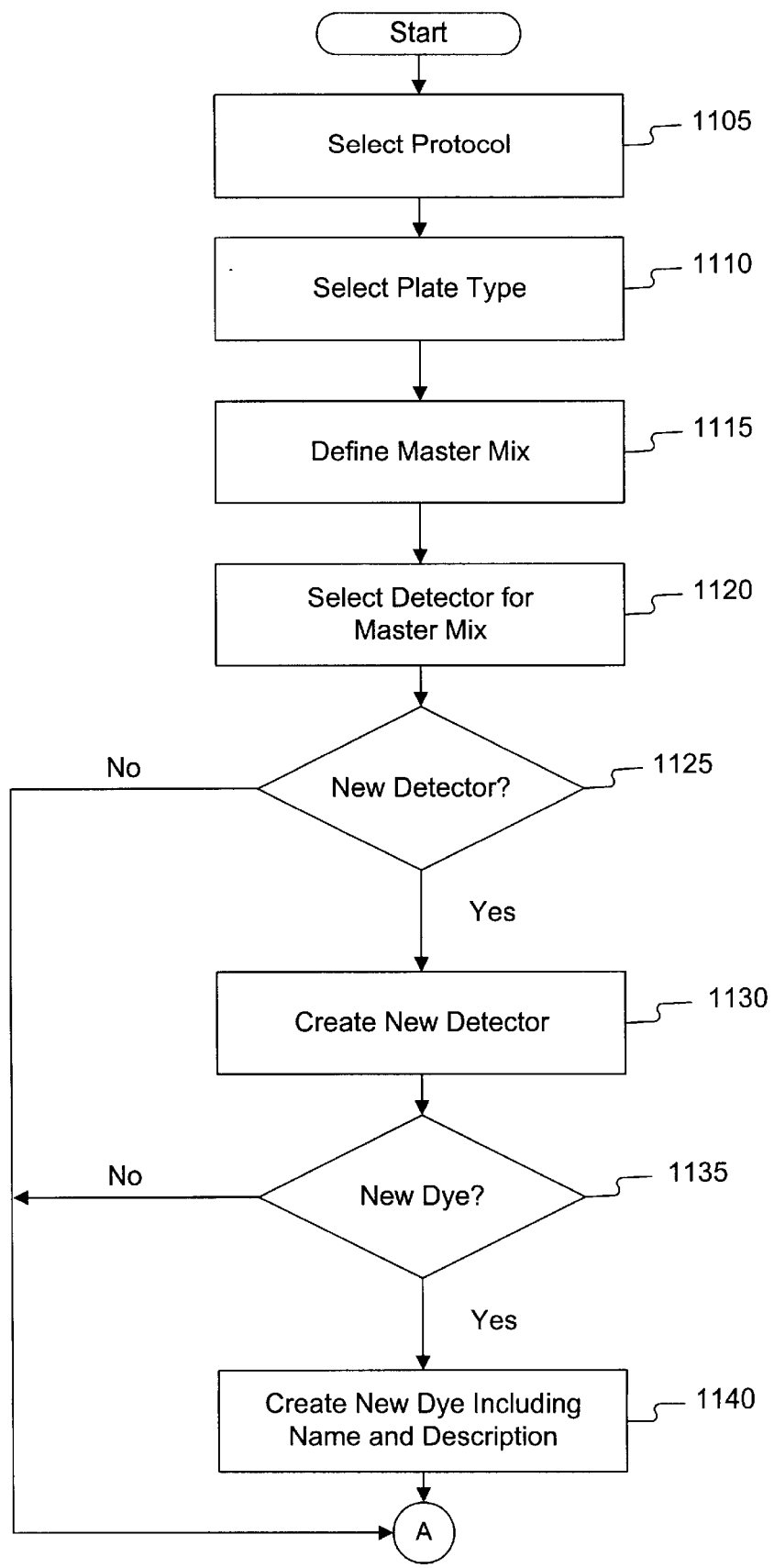
FIGS. 11A and 11B show the steps of a process for creating a new or modified PCR protocol consistent with the present invention.
Figure 11B:
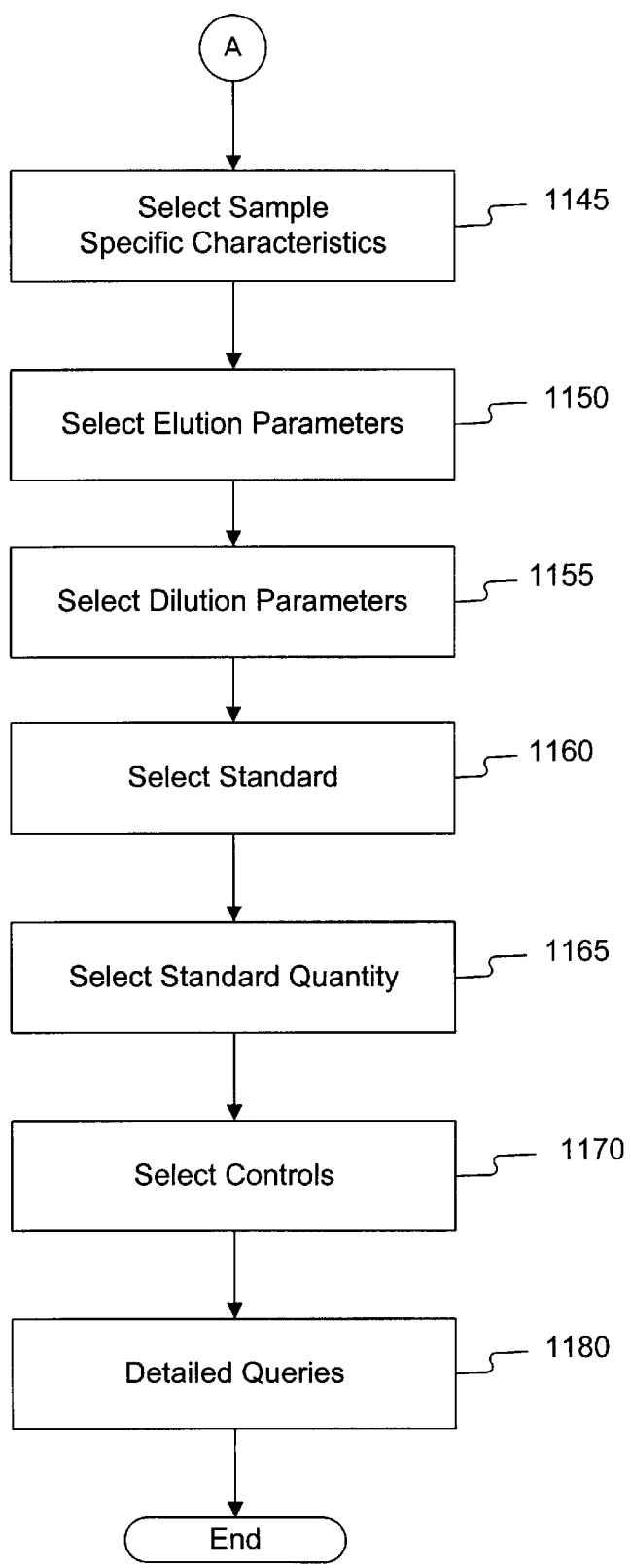
Figure 12:
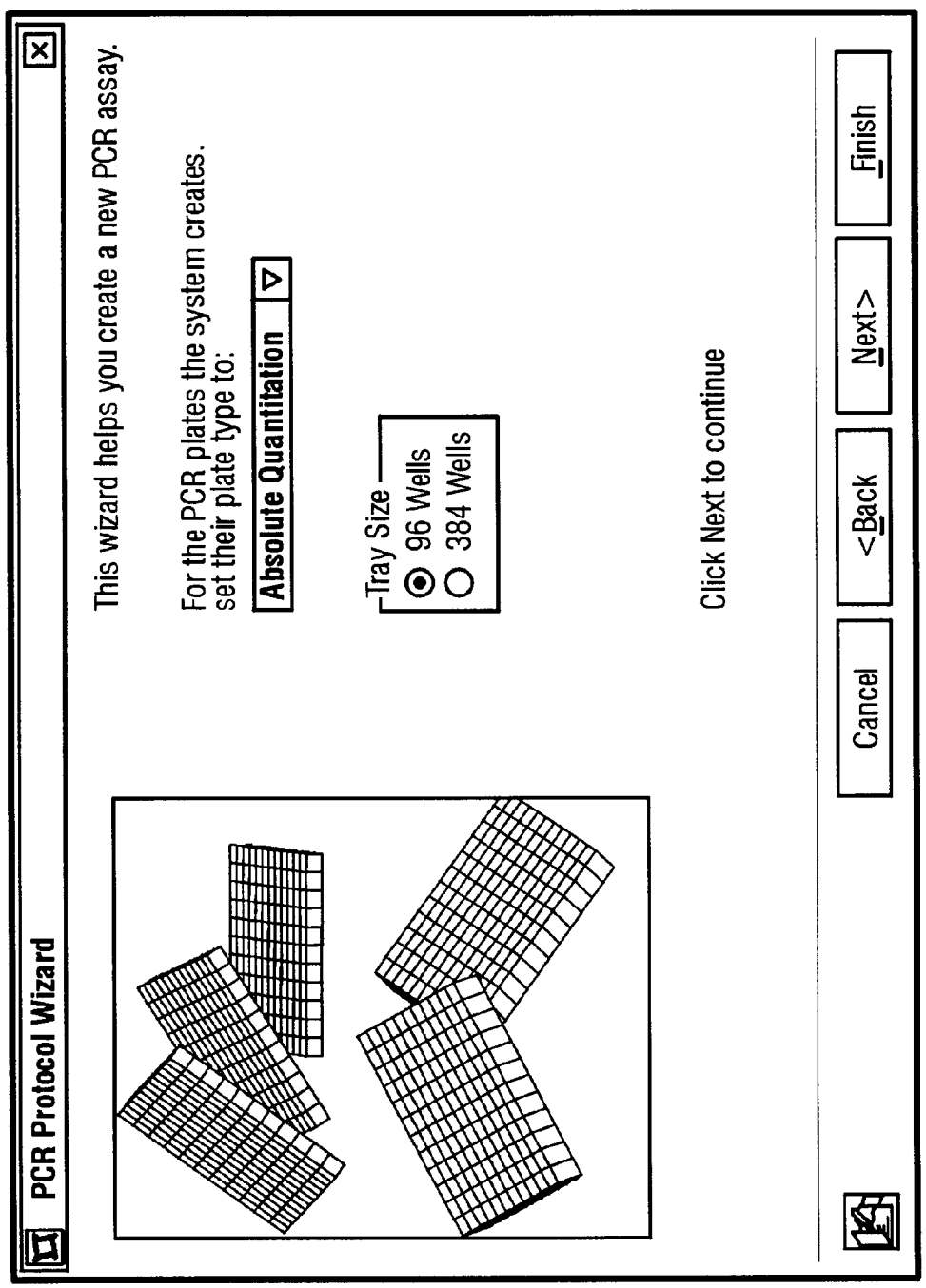
FIG. 12 shows an exemplary GUI consistent with the present invention.

If the user chooses the PCR procedure in step 205 of FIG. 2, the user must select a specific PCR protocol. FIGS. 11A and 11B illustrate the steps of a process for creating a new PCR protocol consistent with the present invention. The user may select a standard protocol from a list of protocols or choose to create a new PCR protocol by entering new parameters or modifying the parameters of an existing protocol (step 1105). If the user chooses to create a new PCR protocol, a GUI as is shown in FIG. 12 may be displayed to the user. The user enters or selects a plate type (step 1110). If the user selects a supported type, the process recalls stored parameters for the selected type and may display them parameters as initial values to the user.

Figure 13:
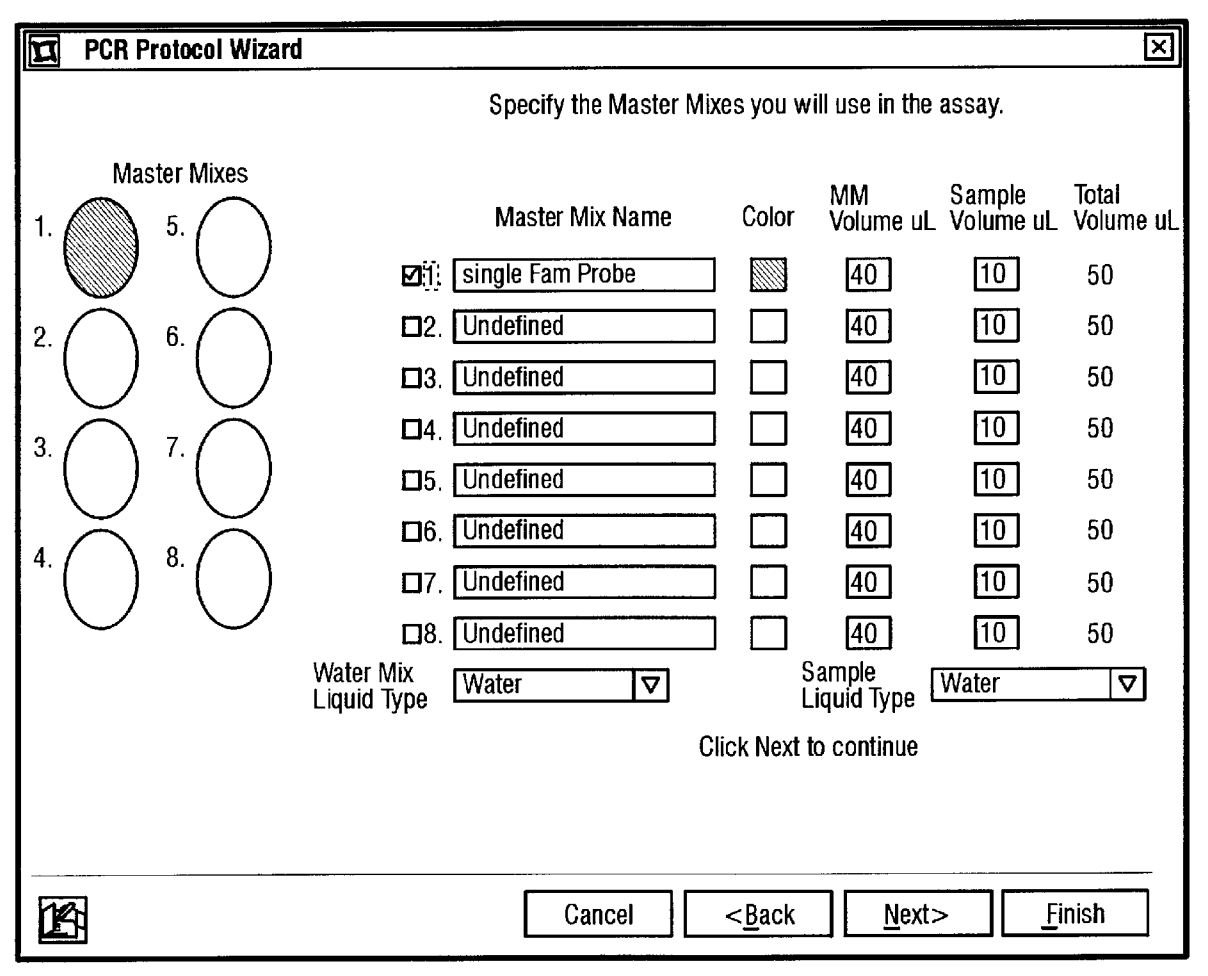

The user also defines all of the master mixes that will be used to do the PCR reaction (step 1115). A master mix is a combination of oligonucleotides (synthetic DNA), optionally with fluorescent dyes attached, enzymes, and various salts in a buffer solution, optionally with an intercalating detector. Master mixes are chosen based on the specific genetic code that the scientist wants to find in the sample. The user defines a master mix by choosing such parameters as master mix name, color or pattern for displaying on the screen, volume of mix, volume of sample to be transferred, and liquid type. FIG. 13 shows a exemplary GUI for use in defining master mixes.

Part of defining a master mix is selecting at least one detector for each master mix (step 1120). A detector is a method of labeling the results of the PCR reaction for monitoring by such means as probe or other suitable techniques. A detector may be, for example, a molecule, such as an intercalator, or a "probe," a short stretch of DNA with fluorescent dyes attached.

Figure 14:
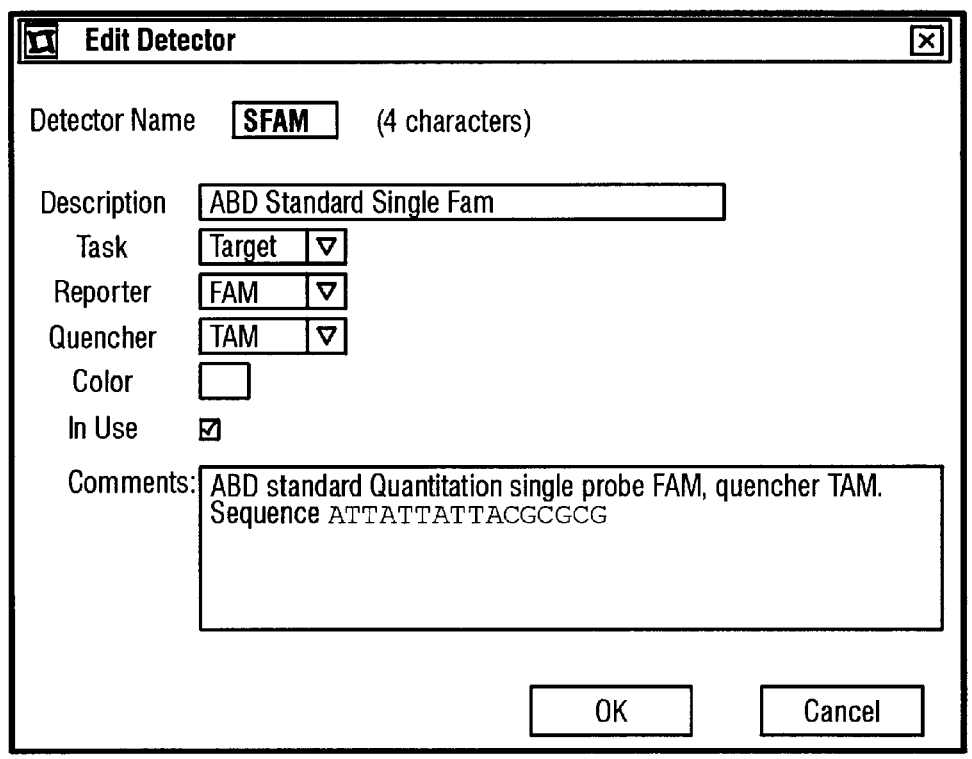
FIG. 14 shows an exemplary GUI consistent with the present invention.

If the user chooses to create a new detector (step 1125), the user specifies such parameters as task, quencher, reporter color, and comments (which should include the sequence) (step 1130). A "quencher" is a molecule which absorbs the light emitted by a fluorescent reporter dye. A "task" may be an Internal Positive Control (IPC), that is, a target for an unknown or a test. If a new detector is chosen, the user can also choose the dye (step 1140), including name and description. FIG. 14 shows an example of a GUI for use in creating or editing a detector.

During PCR, the molecule is cleared and the quencher no longer absorbs the light emitted by the reporter dye. Since the amount of reporter dye which is no longer quenched is directly proportional to the amount of amplified DNA, it may be used to perform real time quantification.

Figure 15:
FIG. 15 shows an exemplary GUI consistent with the present invention.

If the user does not create a new detector (step 1125) or a new dye (step 1135), the process continues with step 1145. The user has the option of modifying the specific parameters for each sample in a tray (step 1145). Consistent with the present invention, the user is able to graphically view each of the output trays and modify one or more samples in the tray. FIG. 15 is a one example of a GUI for graphically displaying PCR trays to the user and how the trays will be produced based on the current chosen parameters. Also displayed may be textual feedback that indicates the maximum number of samples as well as what the limiting factor is. The user may also select to combine one or more output trays into one output tray, a procedure known as "pooling."

Figure 16A:
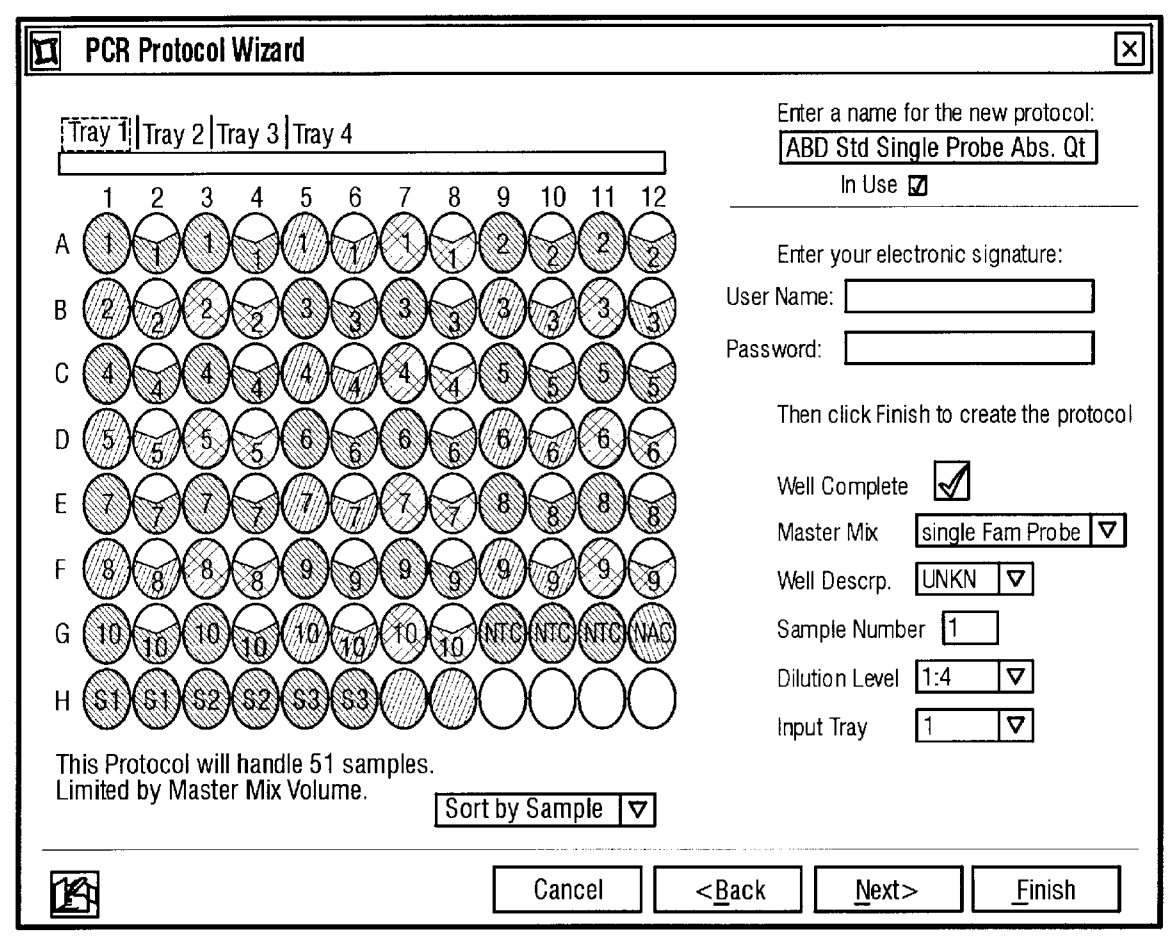
Figure 16B:
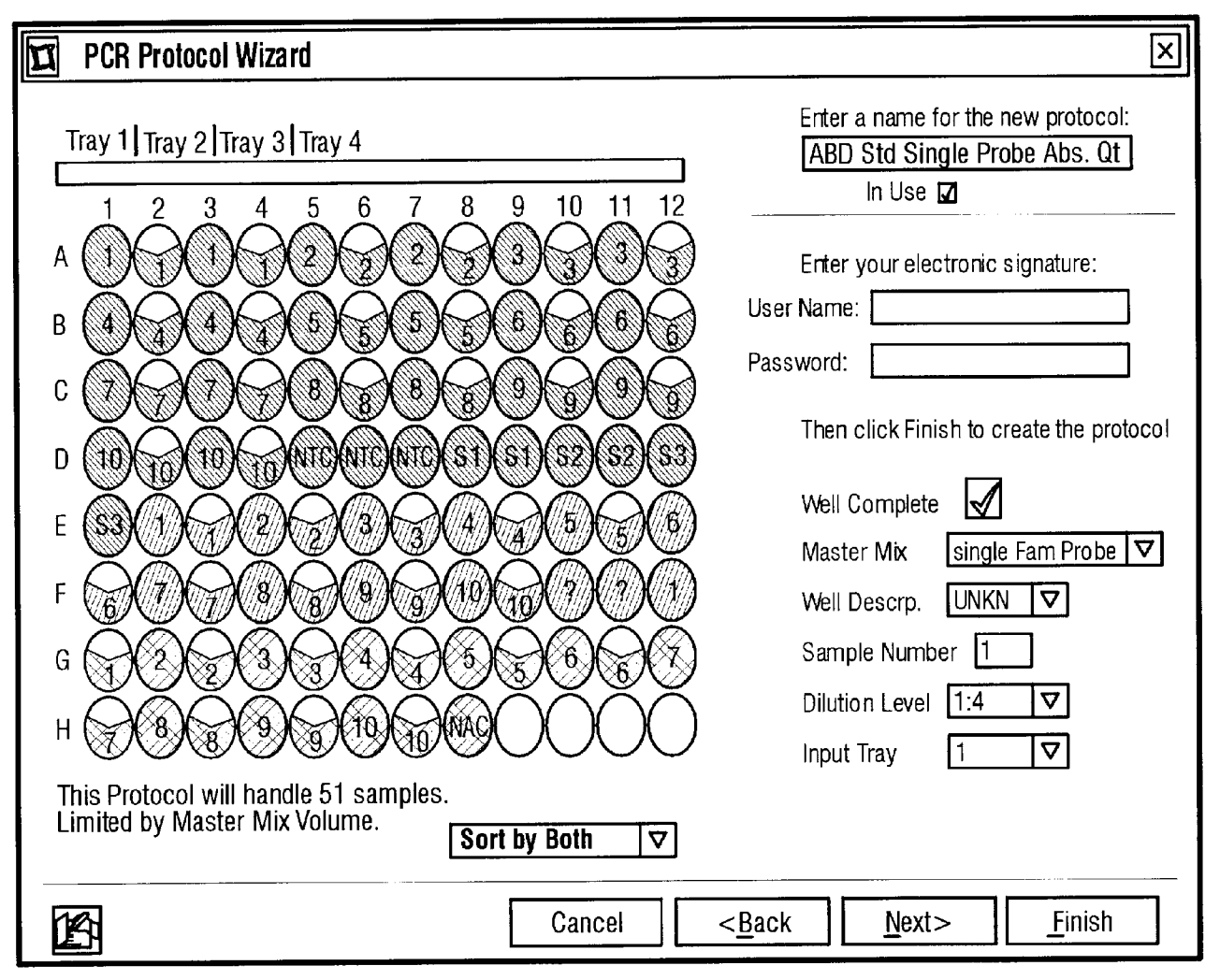
Figure 17A:
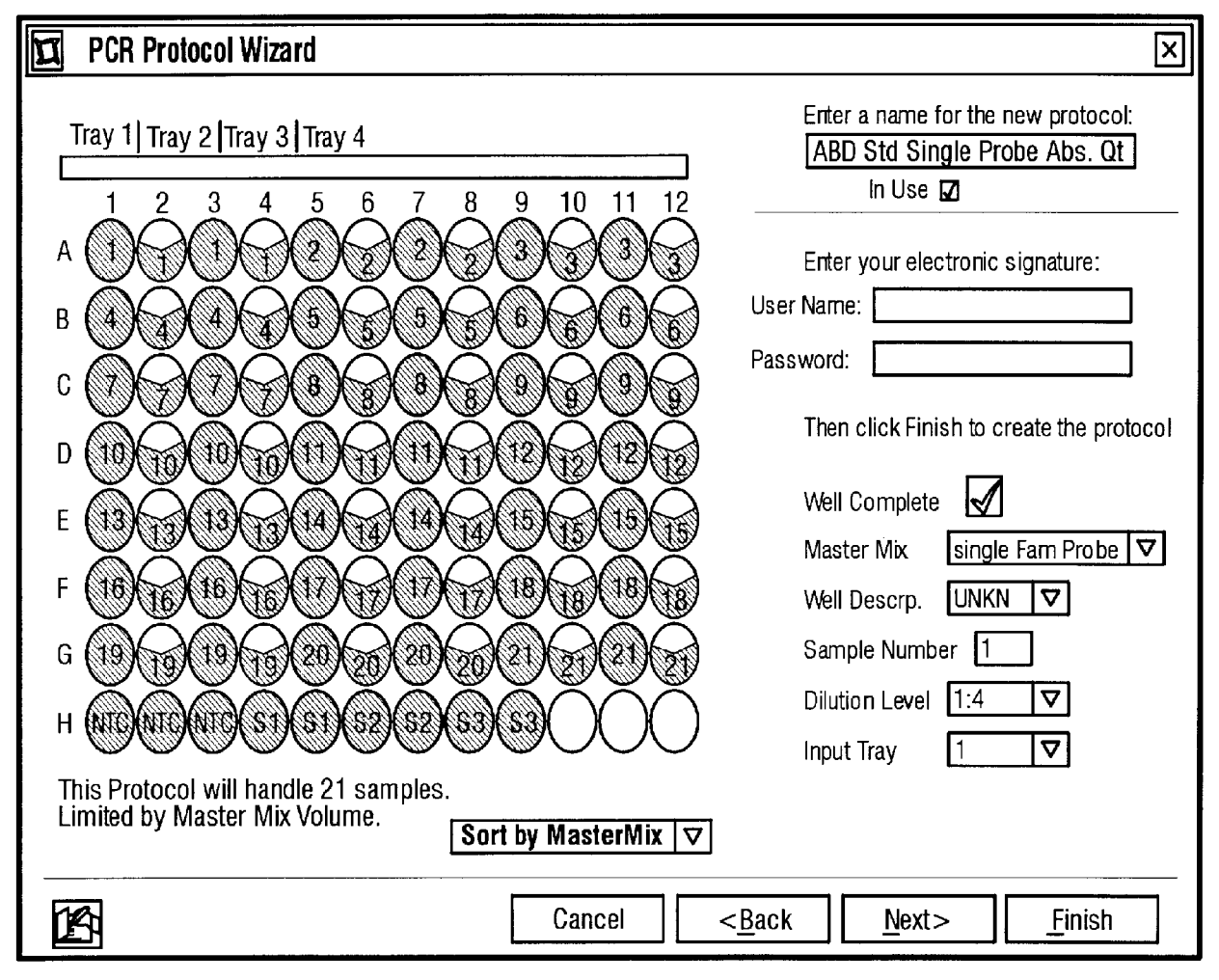
Figure 17B:
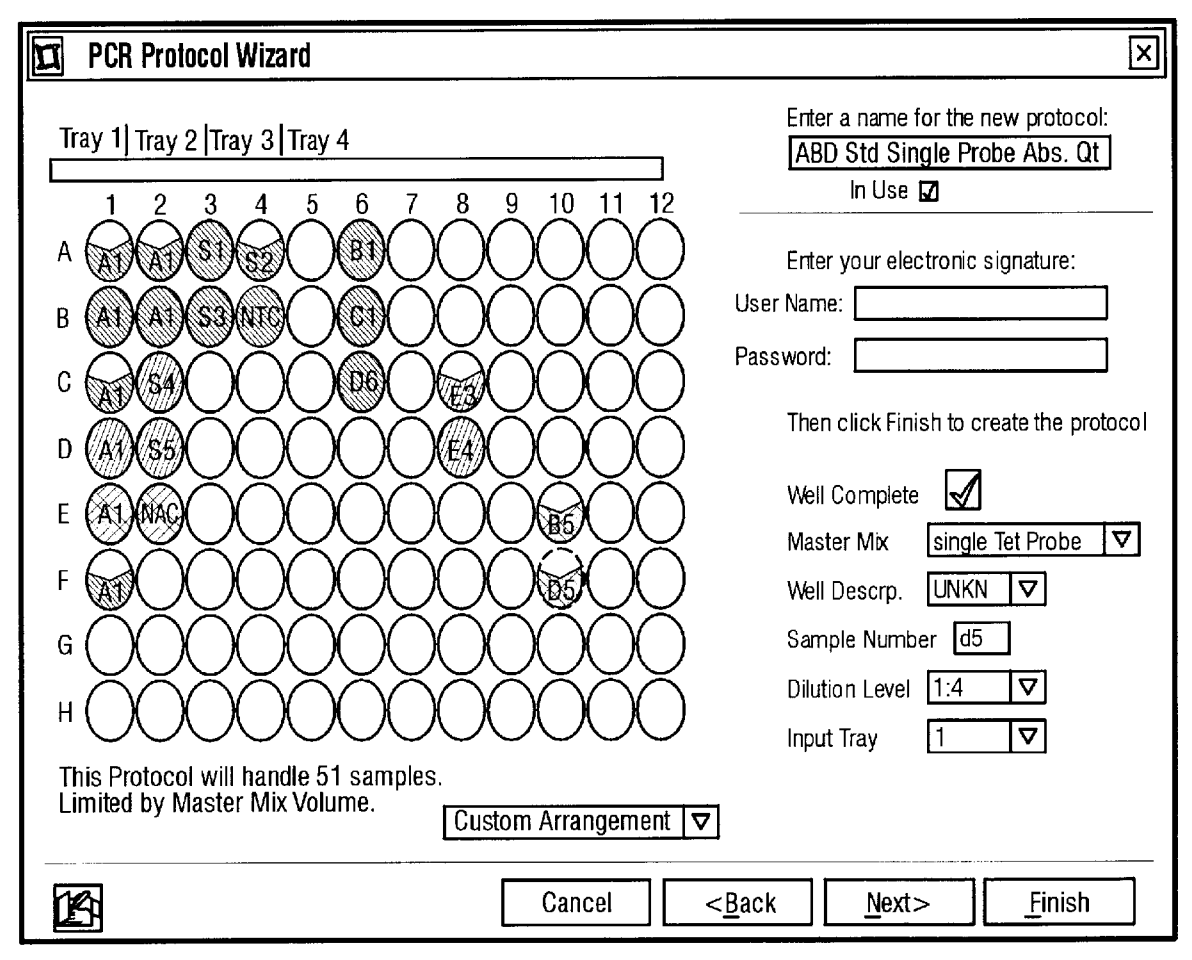

In step 1145, the user defines the parameters for performing PCR on the samples in the input tray. For each sample, the user chooses the number of replicates of each sample for each master mix and also the number of initial mixes for homogenizing the sample prior to transferring the sample to the PCR tray. The user also chooses the number of input trays that this protocol can work from and the way the samples may be sorted. Wells or samples may be sorted, for example, by row, column, or other pattern. The tray arrangement may also be arranged based on both master mix and sample or some other custom arrangement. Typically, other systems allow only one means for sorting samples, typically by master mix, unless done by customized robot. Allowing the user to select a manner for organizing samples facilitates analysis. FIG. 16A shows an exemplary GUI where the samples in the tray are sorted according to sample. This sort method provides the easiest sort method for a typical analysis and prevents PCR variations from affecting quantification for different sequences for a single sample. FIG. 16B shows an exemplary GUI where samples are sorted according to both sample and master mix used. FIG. 17A is an example of a GUI showing the samples sorted according to master mix; FIG. 17B shows a custom arrangement where, within the constraints imposed by the rest of the parameters defined by the user in the PCR protocol, the user may choose the placement of the wells in the tray.

Dilution may be performed as part of the PCR protocol. The user may either select initial, serial, or custom dilution and may indicate which of the resulting dilutions that the user wishes to use (step 1155). Following dilution, the user selects at least one standard based on the master mix in use (step 1160). A standard is a known quantity of a known biological macromolecule. The user may also select the standard quantities or concentration of each detector for each master mix, and number of replicates of DNA to be produced by the PCR procedure (step 1165). Controls for the master mix may also be set by the user (step 1170). In selecting controls, the user may select, for example, no template control ("NTC"), no amplification control ("NAC"), or other optional controls. An NTC is a sample that has no nucleic acids in it and is used to confirm that false positives from contamination or instrument malfunction do not occur. An NTC is usually water or a buffer solution. A NAC has a quantity of the intended target nucleic acid, but also has a component which should inhibit the PCR reaction. An NAC is used to confirm that an instrument malfunction has not occurred.

Finally, the user may make detailed queries as to the contents of any particular well by, for example, clicking on the well (step 1180). The user may select custom parameters by, for example, modifying standard default or previously defined parameters for any one of the wells. If parameters are changed in the protocol such that it would render any of the selected wells invalid, those wells will be deselected and their parameters cleared.

Returning now to FIG. 2, after setting up the parameters for each protocol (step 220), the user prepares the trays by putting a biological material sample into each of the sample wells and inputs information identifying the tray (step 225). The middle column of FIG. 3 shows one method for inputting information. The user may, for example, type in information identifying the tray or plate, such as a number or tray name. The system may also include a bar code reader and the user may enter the tray name by, for example, scanning a bar code. The user may select the tray type from a list of tray types from an external data base. The user also enters identifying information, such as sample name and number, for each well of the tray. As described earlier, a tray may include any number of wells, however, a tray size of 96 or 384 is common.

The tray names or bar codes of the tray and sample input names or bar codes should be unique. Sample input names may be entered manually by the user, selected from a list, or input via a scanning device, such as a bar code reader. Alternatively, the trays and sample can be automatically assigned default names such as, for example, one-up numbers or, optionally, by selecting names from the GUI showing a graphical representation of the sample tray.

When the user has completed the process of entering tray and well information, the system checks for duplicate information (step 230). If an error or duplicate is detected, the system indicates an error and prompts the user to re-input or modify the information (step 225).

The user also may select which of the individual samples in tray will be subjected to each of the chosen procedures. For example, shown on the right hand side of FIG. 3 is a graphical representation of an exemplary 96-well tray. The left hand column of FIG. 3 indicates that the user has chosen to perform three procedures: lysis, archive, and PCR. By indicating the "Lysis" tab, a user may choose which of the wells will undergo the lysis procedure. By indicating the "Archive" tab, the user may choose which of the wells will undergo the archive procedure, and so forth. Some procedures may be sequential, that is, a later-performed procedure operates on the results of earlier procedures. The system therefore may perform checks to ensure that the user selects in later steps only the same wells or a subset of previously chosen wells for later procedures (step 240).

Figure 18:
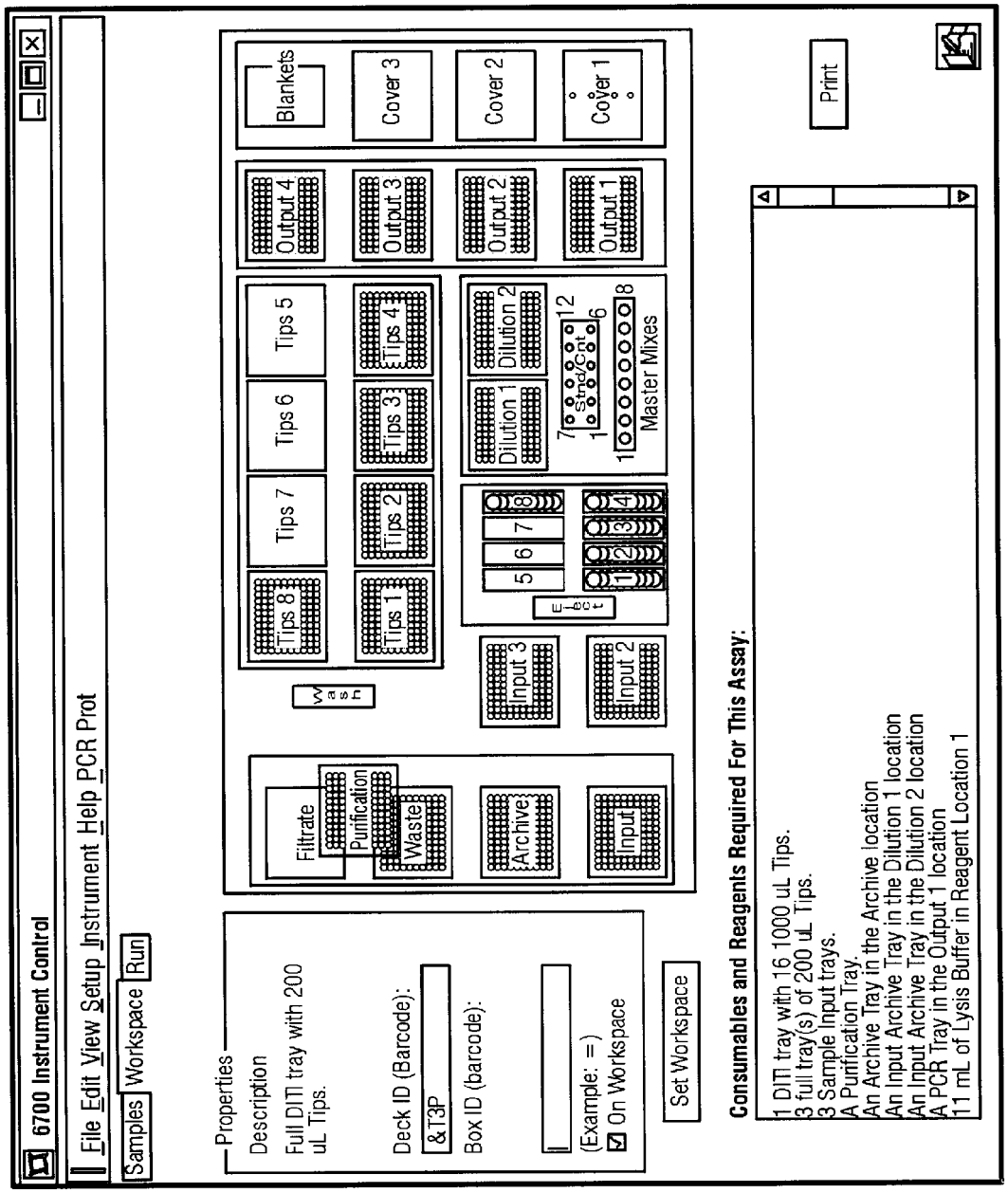
FIG. 18 shows an exemplary GUI consistent with the present invention.

Following user set up of the trays and individual samples, the user may set up the work space (step 245). To assist the user, the system may display to the user a GUI, such as FIG. 18, that represents the work space. The user may use a work space GUI, like FIG. 18, to stock the work space in preparation for executing a run of a software program for performing this process. FIG. 18 is an example of a color-coded GUI representing a laboratory instrument work space showing, for example, all the input trays, representations of required liquids or chemicals, purification trays, different covers or seals, types of disposable tips, and other graphical representations of common work space items. A user may enter information about the work space by, for example, typing in information, clicking on choices presented to a user, operation of a wizard, or scanning the work space, if at least one item in a work space is associated with a bar code. Information on each item in the work space may be recorded and tracked. For example, all individual tips may be bar coded and use of each recorded to ensure compliance with governmental policies. Each item may be color-coded to provide additional information to the user. An item featured in one color may indicate, for example, that the item is empty and needs to be refilled. Another color may indicate, for example, that the item is full and needs to be emptied, or is in an improper position. Textual lists of available reagents and consumables may also be displayed. Any of the items in the work space may be associated with a bar code.

All tray and deck information is checked against earlier information provided by the user and duplicate or erroneous information is identified (step 255). Once the user has finished entering information, the user indicates that they would like to begin the run (step 260). At this point, the user may be required to enter such information as user name, password, and a run name. Alternatively, without a run name, the run may be tracked by an automatically assigned run number. The process then checks to ensure the user has properly entered all required information (step 265). All information, including user name, protocols and bar codes, are all stored in the data base such that every parameters associated with every sample in every tray may be determined. If so, the process begins the run (step 270). During the run, the user may pause or stop the run at various times, or the run may be interrupted by system warnings.

Optionally, the first step in the run is initial sample preparation (step 103). Samples may be prepared in any number of known methods depending on the sample type. Tissue samples may be prepared, for example, by using an ultrasonicator, using a macerator or "bead masher," or subjecting the tissue sample to certain temperatures. If the sample is a fluid, such as blood, for example, sample preparation may involve mixing the sample with chemicals. The goal of the sample preparation step is to create a homogeneous mixture capable of being used by subsequent procedures.

Following initial sample preparation, the biological material samples are ready for lysis (step 105). Based on the lysis protocol chosen or created by the user during the set up process, the system performs the steps of lysis. According to the parameters of the protocol, the system adds the designated lysis buffer to the biological material sample and mixes the mixture the designated number of times. To add the lysis buffer to the sample, pipette tips operated by the system may aspirate reagent and dispense the reagent into the designated well or alloquate reagent into the well from storage tanks. To mix, the mixture is repeatedly aspirated and dispensed back into the well using the pipettes.

If an incubation period is specified following lysis, the trays may be left undisturbed for the specified period and temperature before proceeding to the next step. Also at this point, the process may be terminated (step 110) and the trays manually removed from the system for use or storage (step 115).

Alternatively, the process may begin with step 118 using trays containing lysed cells, or a DNA filtrate, that were previously prepared, either manually or automatically by this system or others. If the archive procedure was chosen in setup (step 101), the archive protocol is performed according to the archive protocol defined or chosen by the user (step 120).

Following the archive protocol, the result may be either a DNA tray, an RNA archive tray, and optionally a DNA filtrate tray, among others. At this point, the process may be terminated (step 125) and the trays manually removed from the system for use or storage (step 130).

Alternatively, the process may begin with step 135 using archive trays that were previously prepared, either manually or automatically by this system or others. If at least one of the input trays at this point consists of an RNA archive tray (step 135), and the choice to "Make cDNA" was specified by the user during setup (step 140), the process may make cDNA according to the parameters defined by the user (step 145). If there no more procedures to be performed are remaining (step 150), the process may be terminated (step 155) and the trays manually removed from the system for use or storage.

Alternatively, the process may begin with step 160 using archive trays that were previously prepared, either manually or automatically by this system or others. If dilution was chosen in setup (step 101), the dilution protocol is performed according to the dilution protocol defined or chosen by the user (step 165). Following dilution, the process may terminate (step 170), and the trays manually removed from the system for use or storage (step 175).

Alternatively, the process may begin with step 180 using archive trays that were previously prepared, either manually or automatically by this system or others. If the PCR procedure was chosen by the user in step 101, the PCR procedure is performed according to the protocol selected or defined by the user (step 180).

In step 185, the trays may be used for data analysis. Data analysis may be performed manually or by other automated systems. The information about any tray may be accessed from a data base in a central server.

Figure 20:
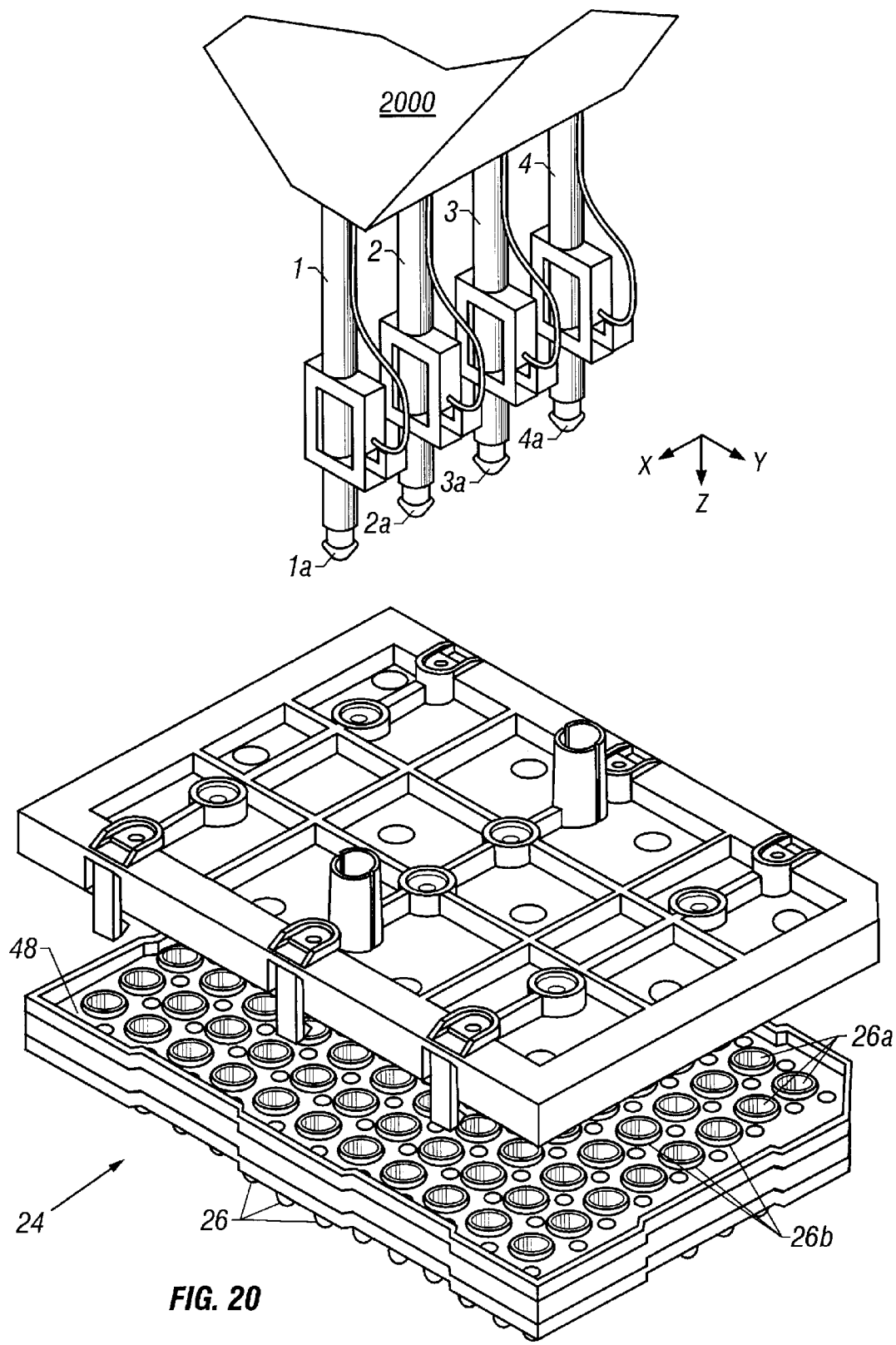
FIG. 20 shows a diagram of a robot consistent with the present invention.

If at any point the process is terminated, steps 115, 130, 155, 175, the tray may be automatically sealed following termination of the protocol, as shown in FIG. 20.

C. System Architecture

Figure 19:
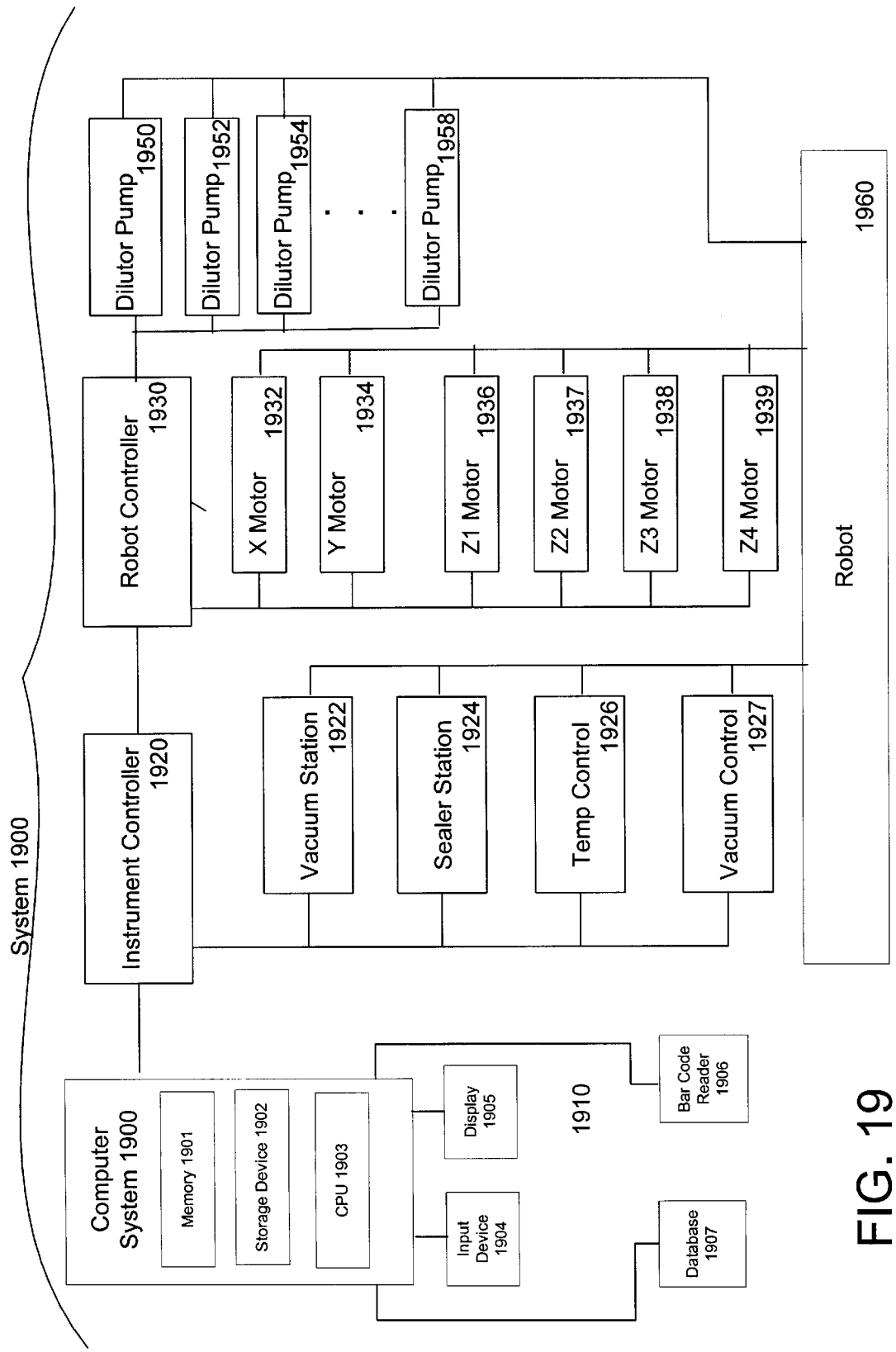
FIG. 19 shows a block diagram of an automated system in which methods, apparatus, and articles of manufacture consistent with the present invention may be implemented.

FIG. 19 depicts an exemplary system 1900 suitable for practicing methods and implementing systems consistent with the present invention. System 1900 includes a computer system 1910 operatively connected to an instrument controller 1920, robot controller 1930, dilutor pumps 1950 through 1958, and a mechanical fluid handling apparatus 1960, also called a robot.

Computer system 1910 is a standard PC or laptop containing a main memory 1901, a secondary storage device 1902, a central processing unit (CPU) 1903 operatively connected to an input device 1904, and a display 1905. Computer system 1910 is also optionally connected to an external database 1907 and bar code reader 1906. Graphical user interfaces, software programs in executable or source code format, and protocol parameters may be stored in main memory 1901 or, optionally, in external database 1907.

Software programs designed in accordance with the present invention consist of program code for performing steps of the present invention.

Computer system 1910 comprises a display 1905, such as a cathode ray tube (CRT) or liquid crystal display (LCD), for displaying information to a computer user. Computer system 1910 also comprises an input device 1904, including alphanumeric and other keys, communicates information and command selections to CPU 1903. Other types of suitable devices for input device 1904 include a mouse, trackball or cursor direction keys for communicating direction information and command selections to CPU 1904 and for controlling cursor movement on display 1905. Bar code reader 1906 may be any conventional device capable of scanning numbers, figures, or other graphics and converting the information to an identifying data package.

Computer system 1910 is a means for receiving parameters from the user and transmitting commands to instrument controller 1920. Computer system 1910 may also be used alone to simulate assay preparation or to pre-prepare protocols for future use. If computer system 1910 is not operatively connected to instrument controller 1920, instructions prepared on computer system 1910 may be stored on disk and transported to instrument controller 1920 or robot controller Instrument controller 1920 is a means for receiving commands from computer system 1910 and distributing the commands to vacuum station 1922, sealer station 1924, temperature control 1926, and vacuum control 1927. Examples of suitable instrument controllers include a PC board with a microcontroller, such as a Motorola G8332, memory for program storage, memory for data storage, R5232 communication devices, and A/D converters with inputs for temperature, vacuum, air flow, humidity, and diagnostic voltages and current sense levels. Additionally, output driver devices which control pumps, solenoids, peltiers, heaters, stepper motors, and indicator lights may be suitable instrument controllers.

Vacuum station 1922 is a mechanism that controls the use of vacuum by robot 1960. Vacuum station 1922 provides, for example, controlled vacuum for use during elution in the protocols described above. The vacuum station is a mechanism which holds and transports a purification tray, providing vacuum seals to the purification tray. The vacuum controller provides a regulated supply of vacuum to any of several chambers of the vacuum station, or the suction cups of the sealing station, or a purification tray cover. It consists of a pump controlled by a microcontroller, valves and manifolds, pressure transducers, and a ballast/waste tank.

Sealer station 1924 is a mechanism used for sealing PCR trays. Vacuum is also used during the sealing process, by creating a vacuum in suction cups that are used to pick up optional blankets and hold them while they are transported to the correct location. The optional blankets are then melted onto the top of the tray in a sealing process. Temperature control 1926 controls the temperature throughout the various stages. Temperature control 1926 may, for example, increase temperature during incubation and sealing and maintain cooler temperatures at other times to prevent sample degradation.

Instrument controller 1920 sends RS232 commands to robot controller 1930. Robot controller 1930 interprets the commands and determines which pump or motor should receive the command. Robot controller 1930 also coordinates activities that involve more than one pump or motor. Robot controller 1930 is a standard microprocessor board. Each of motor 1932 through 1939 and dilutor pumps 1950 through 1958 contain processors that can interpret the commands. Motor 1932 may be, for example, a motor that controls movement of robot 1960 in the x-direction. Motor 1934 may be, for example, a motor that controls movement of robot 1960 in the y-direction. Motors 1936 through 1939 drive corresponding fingers and control movement in the z-direction. Dilutor pumps 1950 through 1958 are motor-driven precision syringe pumps with rotary values. The number of pumps will generally correspond to the number of fingers in robot 1960.

Robot 1960 is an automated motor controlled system designed for fluid handling in a laboratory atmosphere. An exemplary robot is available commercially under the trade name TECAN® RSP from Tecan AG of Hombrechtikon, Switzerland As shown in FIG. 20, a robot, suitable for use with the present invention, includes multiple elongated aspiration and injection fingers, denoted as 2001–4, mounted on a robotic arm 2000 at respective points generally defining a line. Arm 2000 can move the fingers in the x/y direction along a generally horizontal plane in response to commands from motors 1932 and 1934. Each of the fingers 2001–4 can be separately moved in the z direction along a vertical axis in response to commands from the corresponding motor 1936 through 1939. Movement of arm 2000 and fingers 2001–4 is carried out in response to commands transmitted from computer system 1910 to robot controller 1940. Fingers 2001–4 can be used to transfer fluids to and from wells 2026 in tray 2024. Fluids may be transferred through fingers 2001–4 to wells 26 during, for example, for the purposes of adding reagents, dilution, and mixing.

One example of an automated apparatus suitable for use with the present invention is the apparatus described in U.S. patent application Ser. No. 09/182,946, to Moring et al., filed Oct. 29, 1998, which is expressly incorporated herein by reference.

Although aspects of one implementation are depicted as being stored in memory 1920, one skilled in the art will appreciate that all or part of systems and methods consistent with the present invention may be stored on or read from other computer-readable media, such as secondary storage devices, like hard disks, floppy disks, and CD-ROM; a carrier wave received from a network such as the Internet; or other forms of ROM or RAM. Finally, although specific components of System 1900 have been described, one skilled in the art will appreciate that a System suitable for use with methods and systems consistent with the present invention may contain additional or different components.

D. Conclusion

As described in detail above, methods, apparatus, graphical user interfaces, and articles of manufacture consistent with the present invention perform automated biological assay preparation and automated biological macromolecule purification. The foregoing description of an implementation of the invention has been presented for purposes of illustration and description. For example, the described implementation includes software but the present invention may be implemented as a combination of hardware and software or in hardware alone. Furthermore, the present invention has been described using exemplary parameters, graphical user interfaces, and techniques for receiving user input, but is not intended to be limited to the parameters used. The scope of the invention is therefore defined by the claims and their equivalents.

What is claimed is:

1. A computer-implemented method for performing automated sample processing, wherein the sample processing is performed on an automated laboratory work station including a robot, the method comprising:

receiving a first set of user-specified protocol parameters;

receiving a second set of user-specified protocol parameters;

comparing the first set of user-specified protocol parameters to the second set of user-specified protocol parameters to identify incompatibility;

modifying the first or second set of protocol parameters to correct the incompatibility;

manipulating the robot to perform a first procedure on a first sample tray in response to computer instructions based on the modified first set of protocol parameters to obtain a second sample tray;

without intermediate human intervention following performance of the first procedure, manipulating the robot to perform a second procedure on the second sample tray in response to computer instructions based on the modified second set of protocol parameters; and outputting the second sample tray comprising a result following the automated sample processing.

2. The computer-implemented method of claim 1, further comprising:

storing the modified first and second sets of protocol parameters such that they can not be modified.

3. The computer-implemented method of claim 2, further comprising:

automatically modifying the first or second set of protocol parameters to eliminate the incompatibility.

4. A computer-implemented method for performing automated sample processing wherein the sample processing is performed on an automated laboratory work station including a robot, comprising:

permitting a user to specify a first set of protocol parameters for controlling the robot to perform a first protocol on a first sample tray to obtain a second sample tray; and specify a second set of protocol parameters for controlling the robot to perform a second protocol on the second sample tray without additional human instruction following completion of the first protocol, wherein the second protocol is different from the first protocol; and displaying representations of the first and second sample trays showing graphically the protocol to be performed on each well of the first and second sample trays.

5. The computer-implemented method of claim 4, further comprising:

comparing the first and second sets of protocol parameters to identify incompatibilities.

6. The computer-implemented method of claim 5, further comprising:

permitting the user to modify the first or second set of protocol parameters to eliminate the incompatibility.

7. The computer-implemented method of claim 4, further comprising:

alerting the user to incompatibilities between the first and second sets of protocol parameters.

8. An automated sample processing system including a user interface for inputting and displaying protocol parameters, the user interface comprising:

a first view configured to receive instructions defining a first protocol with multiple parameters;

a second view configured to receive instructions defining a second protocol with multiple parameters, wherein the second protocol is different from the first protocol, wherein the instructions defining the first and second protocols manipulate a robot to perform the second protocol immediately following completion of the first protocol and without intermediate instruction from a user; and a third view configured to display representations of a first and a second sample tray showing graphically the first and second protocol to be performed on each well of the first and second sample trays.

9. The automated sample processing system of claim 8, the user interface further comprising:

a fourth view configured to receive instructions for modifying the first or second protocols to eliminate incompatibilities between the protocols parameters.

10. A computer-readable medium containing instructions for controlling a robot to perform a method for automated sample processing, the method comprising the steps of:

displaying a first view configured to receive instructions defining a first protocol with multiple parameters;

displaying a second view configured to receive instructions defining a second protocol with multiple parameters, wherein the second protocol is different from the first protocol, wherein the instructions defining the first and second protocols manipulate the robot to perform the second protocol immediately following completion of the first protocol and without intermediate instruction from a user; and displaying a third view configured to display representations of a first and a second sample tray showing graphically the first and second protocol to be performed on each well of the first and second sample trays.

11. The computer-readable medium containing instructions for controlling a robot to perform a method for automated sample processing of claim 10, the method further comprising the step of:

displaying a fourth view configured to receive instructions for modifying the first or second protocols to eliminate incompatibilities between the protocols parameters.

12. An apparatus for performing automated sample preparation, the apparatus comprising:

a robot;

processor configured to:

receive a first set of user-specified protocol parameters defining a first procedure;

receive a second set of user-specified protocol parameters defining a second procedure;

compare the first set of user-specified protocol parameters to the second set of protocol parameters to identify incompatability;

modifying the first or second sets of protocol parameters to correct any identified incompatability;

means for converting the modified first and second set of protocol parameters into program instructions; and transmitting the program instructions to a robot controller; a memory for storing program instructions, and a robot controller configured to use the program instructions to:

manipulate the robot to perform in response to program instructions based on the modified first set of protocol parameters the first procedure on a first sample tray to obtain a second sample tray; and without intermediate human intervention following the first procedure, manipulate the robot to perform in response to program instructions based on the modified second set of protocol parameters the second procedure on the second sample tray to obtain a third sample tray, wherein the second procedure is different from the first procedure.

13. A computer-implemented method for performing automated sample processing, wherein the sample procedures are performed on an automated laboratory work station including a robot, the method comprising:

receiving a set of user-specified protocol parameters;

checking the set of protocol parameters for incompatability between parameters in the set of protocol parameters;

modifying the set of protocol parameters to correct the incompatibility;

manipulating the robot to perform a procedure on a sample tray in response to computer instructions based on the modified set of protocol parameters; and outputting the sample tray comprising a result of the automated sample processing.

14. A computer-readable medium containing instructions for controlling a robot to perform a method for automated sample processing, the method comprising the steps of:

receiving a first set of user-specified protocol parameters;

receiving a second set of user-specified protocol parameters;

comparing the first set of user-specified protocol parameters to the second set of user-specified protocol parameters to identify incompatibility;

manipulating the robot to perform a first procedure on a first sample tray in response to computer instructions based on the modified first set of protocol parameters to obtain a second sample tray; and without intermediate human intervention following performance of the first procedure, manipulating the robot to perform a second procedure on the second sample tray in response to computer instructions based on the modified second set of protocol parameters.

15. A computer-implemented method for performing automated sample processing, wherein the sample processing is performed on an automated laboratory work station including a robot, the method comprising:

receiving a first set of user-specified protocol parameters;

receiving a second set of user-specified protocol parameters;

comparing the first set of user-specified protocol parameters to the second set of user-specified protocol parameters to identify incompatibility;

alerting a user to incompatabilities;

manipulating the robot to perform a first procedure on a first sample tray in response to computer instructions based on a modified first set of protocol parameters to obtain a second sample tray; and without intermediate human intervention following performance of the first procedure, manipulating the robot to perform a second procedure on the second sample tray in response to computer instructions based on a modified second set of protocol parameters; and outputting the second sample tray comprising a result of the automated sample processing.

16. A computer-implemented method for performing automated sample processing, wherein the sample procedures are performed on an automated laboratory work station including a robot, the method comprising:

receiving a set of protocol parameters;

checking the set of protocol parameters for incompatability between parameters within a protocol;

alerting a user to incompatabilities;

manipulating the robot to perform a procedure on a sample tray in response to computer instructions based on a modified set of protocol parameters and;

outputting the sample tray, wherein the sample tray comprises the result following the procedure.

17. A computer-readable medium containing instructions for controlling a robot to perform a method for automated sample processing, the method comprising the steps of:

receiving a first set of user-specified protocol parameters;

receiving a second set of user-specified protocol parameters;

comparing the first set of user-specified protocol parameters to the second set of user-specified protocol parameters to identify incompatibility;

alerting a user to incompatabilities;

manipulating the robot to perform a first procedure on a first sample tray in response to computer instructions based on a modified first set of protocol parameters to obtain a second sample tray; and without intermediate human intervention following performance of the first procedure, manipulating the robot to perform a second procedure on the second sample tray in response to computer instructions based on a modified second set of protocol parameters.

18. An apparatus for performing automated sample preparation, the apparatus comprising:

a robot;

a processor configured to:
  receive a first set of user-specified protocol parameters;
  receive a second set of user-specified protocol parameters;
  compare the first set of user-specified protocol parameters to the second set of user-specified protocol parameters to identify incompatibility;
  alert a user to incompatabilities;
  accept user modifications to the first or second set of protocol parameters;
  means for converting the modified first and second set of protocol parameters into program instructions; and
  transmitting the program instructions to a robot controller;

a memory for storing program instructions, and a robot controller; configured to use the program instructions to:
  manipulate the robot to perform in response to program instructions based on the modified first set of protocol parameters the first procedure on a first sample tray to obtain a second sample tray; and
  without intermediate human intervention following the first procedure, manipulate the robot to perform in response to program instructions based on the modified second set of protocol parameters the second procedure on the second sample tray to obtain a third sample tray, wherein the second procedure is different from the first procedure.

* * * * *

UNITED STATES PATENT AND TRADEMARK OFFICE
CERTIFICATE OF CORRECTION

PATENT NO. : 6,326,147 B1  Page 1 of 1
DATED : December 4, 2001
INVENTOR(S) : Mark Floyd Oldham and Peter Carlton Honebein It is certified that error appears in the above-identified patent and that said Letters Patent is hereby corrected as shown below:

<u>Column 16, claim 12,</u>
Line 44, "processor configured" should read -- a processor configured --.

Signed and Sealed this

Twenty-sixth Day of March, 2002

*Attest:*

*Attesting Officer*

JAMES E. ROGAN
*Director of the United States Patent and Trademark Office*